(12) United States Patent
Angelsen et al.

(10) Patent No.: US 11,275,006 B2
(45) Date of Patent: Mar. 15, 2022

(54) ULTRASOUND ESTIMATION OF NONLINEAR BULK ELASTICITY OF MATERIALS

(71) Applicant: SURF Technology AS, Trondheim (NO)

(72) Inventors: Bjorn A. J. Angelsen, Trondheim (NO); Johannes Kvam, Oslo (NO); Stian Solberg, Florvåg (NO)

(73) Assignee: SURF Technology AS, Trondheim (NO)

( * ) Notice: Subject to any disclaimer, the term of this patent is extended or adjusted under 35 U.S.C. 154(b) by 0 days.

(21) Appl. No.: 16/717,938

(22) Filed: Dec. 17, 2019

(65) Prior Publication Data
US 2020/0191690 A1     Jun. 18, 2020

Related U.S. Application Data

(60) Provisional application No. 62/780,810, filed on Dec. 17, 2018.

(51) Int. Cl.
*G01N 3/40* (2006.01)
*A61B 8/08* (2006.01)

(52) U.S. Cl.
CPC .............. *G01N 3/405* (2013.01); *A61B 8/485* (2013.01)

(58) Field of Classification Search
CPC ................................ G01N 3/405; A61B 8/485
USPC .... 73/573, 78; 600/437, 438, 440–442, 458; 702/19, 33, 36, 113, 127; 250/358.1, 250/359.1, 360.1; 181/126
See application file for complete search history.

(56) References Cited

U.S. PATENT DOCUMENTS

| | | | |
|---|---|---|---|
| 8,038,616 B2 | 10/2011 | Angelsen et al. | |
| 9,939,413 B2 | 4/2018 | Angelsen et al. | |
| 2006/0052699 A1 | 3/2006 | Angelsen et al. | |
| 2009/0178483 A1 | 7/2009 | Angelsen et al. | |

(Continued)

FOREIGN PATENT DOCUMENTS

WO    WO 2013/051943    4/2013

OTHER PUBLICATIONS

Search Report and Written Opinion dated Jun. 15, 2020 issued in International Patent Application No. PCT/IB2019/001329.

(Continued)

*Primary Examiner* — Robert R Raevis
(74) *Attorney, Agent, or Firm* — Cozen O'Connor

(57) ABSTRACT

Methods and instrumentation for estimation of nonlinear bulk elasticity parameters (NEP) of a material through measuring nonlinear propagation delays (NPDs) at a set of multiple range cells along at least one transmit beam axis, and adapting said NEPs to minimize a functional of the NEPs. The method calculates a distance between a model of the NPDs with the NEPs as input and the measured NPDs, and estimated NEPs are obtained at the minimum of the functional. The NPDs are measured by transmitting at least two pulse complexes comprising a low frequency (LF) and a high frequency (HF) pulse with differences in the LF pulse, along at least one common LF and HF transmit beam axes, and gating out HF receive signals from a multitude of depth ranges along said at least one HF transmit beam axis, and comparing the HF receive signals from two pulse complexes with difference in the LF pulse for each depth range.

19 Claims, 10 Drawing Sheets

(56) References Cited

U.S. PATENT DOCUMENTS

| | | |
|---|---|---|
| 2010/0036244 A1 | 2/2010 | Angelsen et al. |
| 2010/0249590 A1 | 9/2010 | Kanayama et al. |
| 2012/0095699 A1 | 4/2012 | Angelsen et al. |
| 2014/0150556 A1* | 6/2014 | Angelsen ............ G01S 7/52077 73/627 |
| 2019/0009111 A1* | 1/2019 | Myhr ................... A61B 8/0858 |
| 2019/0235076 A1 | 8/2019 | Angelsen et al. |

OTHER PUBLICATIONS

Notice of Allowance dated Nov. 12, 2021 issued in related U.S. Appl. No. 16/258,251.
Office Action dated Jun. 4, 2021 issued in related U.S. Appl. No. 16/258,251.
Myhre "Speeding up SURF Imaging", Sep. 2013.
Hussain "Evaluation of Cross-Beam Vector Doppler Ultrasound Systems For Accurate 3-D Velocity Measurements", IEEE Ultrasonics Symposium, 2012.

* cited by examiner

ULTRASOUND ESTIMATION OF NONLINEAR BULK ELASTICITY OF MATERIALS

RELATED APPLICATIONS

This application claims priority from U.S. Provisional Patent Application Ser. No. 62/780,810 which was filed on Dec. 17, 2018, the entire content of which is incorporated herein by reference.

1. FIELD OF THE INVENTION

The present invention is directed to methods and instrumentation for imaging of linear and nonlinear propagation and scattering parameters of an object using transmission of dual frequency pulse complexes composed of a high frequency (HF) and low frequency (LF) pulse. Imaging with acoustic pressure waves is shown as an example, but the methods are also useful for imaging with shear elastic waves and coherent electromagnetic waves. Applications of the invention are for example, but not limited to, medical imaging and therapy, non-destructive testing, industrial and biological inspections, geological applications, SONAR and RADAR applications.

2. DISCUSSION OF RELATED ART

The fundament of image based tissue characterization is first to estimate the material parameters involved in forming the images, followed by a correlation between these tissue parameters and tissue type and disease. Ultrasound are elastic pressure waves which occur from a cyclic exchange between kinetic and elastic energy. The physical parameters for elastic waves are hence mass density, elastic stiffness parameters and power absorption parameters. The elastic energy is of two types i) pressure bulk compression stiffness that supports p-waves, and ii) shear/deformation stiffness which supports s-waves.

Soft tissue comprises ~65% of water within a structure of larger biomolecules. The mass densities of the larger biomolecules are close to that of water, so that the mass density varies only ±5% between different types of tissues. The low amplitude, linear bulk stiffness of the biomolecules that affects propagation velocity is also close to that of water so that the velocity varies only ±5% around that of water, ~1500 m/s. Ultrasound power absorption has the largest variation of ±20% between tissue types.

Quantitative imaging of ultrasound velocity and absorption requires transmission of the ultrasound through the object in 180 degrees of directions, followed by computer tomographic reconstruction of quantitative images of propagation velocity and power absorption. This is only possible for the breast (potentially also testicles) and requires high processing capabilities. The low variation (±5%) of the linear bulk elasticity parameter requires accurate measurements for tissue characterization, which is a challenge.

Soft tissues do however also have a considerable nonlinear bulk elasticity, where tissue compression makes the material stiffer with an increase in the ultrasound propagation velocity, and tissue expansion makes the tissue softer with a decrease in the velocity. To the $1^{st}$ order, the ultrasound velocity depends on the pressure as $$c(\underline{r}, p) = c_0(\underline{r})[1 + \beta(\underline{r})p] \quad (1)$$

$$c_0(\underline{r}) = \frac{1}{\sqrt{\rho_0(\underline{r})\kappa_s(\underline{r})}}$$

-continued $$\beta(\underline{r}) = \beta_n(\underline{r})\kappa_s(\underline{r})$$

$$\beta_n(\underline{r}) = \left(1 - \frac{B(\underline{r})}{2A(\underline{r})}\right)$$

$$A(\underline{r}) = \rho_0\left(\frac{\partial p}{\partial \rho}\right)_{0,S} = \frac{1}{\kappa_s(\underline{r})}$$

$$B(\underline{r}) = \rho_0^2\left(\frac{\partial^2 p}{\partial \rho^2}\right)_{0,S}$$

where $c_0(\underline{r})$ is the linear low amplitude propagation velocity, p is the local acoustic pressure, and $\beta(\underline{r})$ is the nonlinear elasticity parameter (NEP) that varies ±30% between different types of tissues, shown in FIG. 1 from Prior Art, U.S. patent application Ser. No. 16/259,251. Mass density of uncompressed material is $\rho_0(\underline{r})$, the isentropic volume compressibility is $\kappa_s(\underline{r})$, $\beta_n(\underline{r})$ is a nonlinearity parameter. A and B are the commonly used material parameters defined for example in U.S. patent application Ser. No. 16/259,251. The parameters all depends on the spatial position vector $\underline{r}$ due to spatial variations of the type of material in the tissue.

This figure shows the value distributions of the NEP for fatty, 101, glandular, 102, and connective, 103, tissues in female breasts. The vector $\underline{r}$ represents spatial position in the tissue. A and B are commonly defined bulk elasticity parameters and $\kappa$ is the bulk compressibility of the tissue.

Shear/deformation stiffness is zero for fluids like water. The shear stiffness of soft tissue is hence determined by the structure of the bio-molecular matrix that shapes the soft tissue, and is low with a large variation between different types of tissues. A solid tumor often has higher shear stiffness than surrounding tissue, making it feel as a lump. The shear wave velocity varies within ~2-20 m/s (±90%). The low velocity is not suitable for shear waves to be directly used for imaging.

Estimation of shear stiffness is the target of elastography where external pushing of tissue is used to produce shear deformation of deeper tissue. The movement of the deeper tissue is measured with ultrasound, and this movement is used to estimate the local strain that gives an indication of spatial variations of the shear stiffness and for example detect regions of increased shear stiffness, indicating diseased tissue. Internal sources of tissue shear deformation, like the beating heart, has also been studied.

Elastography does not provide quantitative values of shear stiffness, as the local shear stresses are not known. The shear wave velocity $c_s$ depends on the shear stiffness $\mu$ as $$c_s(\underline{r}) = \sqrt{\mu(\underline{r})/\rho(\underline{r})} \quad \mu(\underline{r}) = \rho(\underline{r})c_s(\underline{r})^2 \quad (2)$$

where $\rho(\underline{r}) \approx 10^3$ kg/m$^3$ is the local tissue mass density. Measurement of shear wave velocity can be done by ultrasound imaging of the particle vibration velocity of shear waves in a method called shear wave imaging. This method allows estimation of spatial variation of propagation velocity of shear waves and hence shear stiffness in local regions (see reference [17] in the reference list below). Numbers shown in brackets [ ] are listed below. The shear waves can be generated by ultrasound radiation force at a depth in the tissue, and external vibrations of the tissue. Internal sources of shear waves, like rapid closure of heart valves, have also been studied for generation of deeper shear waves. The method has found use in detection and characterization of breast cancer, and is being tested for targeting of a reduced number of biopsies for prostate cancer, but conclusive results are not yet established.

The nonlinear bulk stiffness is largely determined by atomic/molecular distance potential, while the shear stiffness is largely determined by the structure of the biomolecular matrix. The two parameters are hence complementary, where combination is interesting for improved tissue characterization, similarly to combining different MR parameters. For example, early prostate cancer gives small changes in shear stiffness, and imaging of the nonlinear bulk stiffness $\beta_p$ might hence be useful for earlier detection of prostate cancer.

Several noninvasive measurements for local elastic stiffness parameters and absorption in deep tissues are found as spatial integrals of the actual material parameters plus considerable measurement noise. Estimation of the local elastic stiffness parameters and also absorption hence requires differentiation of noise measurement signals, which is a challenge. The current invention presents new methods and instrumentation for estimation of differentials of noisy measurements to produce local estimates of the material parameters.

3. SUMMARY OF THE INVENTION

This summary gives a brief overview of components of the invention and does not present any limitations as to the extent of the invention, where the invention is solely defined by the claims appended hereto.

An embodiment of the current invention provides methods and instrumentation for estimation and imaging of linear and nonlinear propagation and scattering parameters in a material object where the material parameters for wave propagation and scattering has a nonlinear dependence on the wave field amplitude. The methods have general application for both acoustic and shear elastic waves such as found in SONAR, seismography, medical ultrasound imaging, and ultrasound nondestructive testing, and also coherent electromagnetic waves such as found in RADAR and laser imaging. In the description below one uses acoustic waves as an example, but it is clear to anyone skilled in the art how to apply the methods to elastic shear waves and coherent electromagnetic waves.

In its broadest form, the invention concerns the transmitting of at least two pulse complexes composed of co-propagating low frequency (LF) and high frequency (HF) pulses along at least one LF and HF transmit beam, where said HF pulse propagates close to the crest or trough of the LF pulse along at least one HF transmit beam, and where one of the amplitude and polarity of the LF pulse varies between at least two transmitted pulse complexes, where the amplitude of the LF pulse can be zero for a pulse complex and the amplitude of at least one LF pulse of said at least two transmitted pulse complexes is non-zero.

Scattered HF pulse components are picked up by one or both of i) a HF backscatter receive beam with close to the same beam axis as the HF transmit beam, and ii) a set of HF receive cross-beams that crosses the HF transmit beam at a multitude of depths along the HF transmit beam axis. HF receive signals from a multitude of depths along the HF transmit beam axis are obtained by one or both i) gating the HF backscatter receive signal around said multitude of depths, and ii) gating the HF receive signals for said set of HF receive cross-beams around the crossing of the HF transmit beam at said multitude of depths.

The HF receive signals from at least two transmitted pulse complexes are compared are compared for each said multitude of depths to form measured values of the non-linear propagation delay (NPD) at said multitude of depths along said at least one HF transmit beam axis. The measured NPDs has lowest sensitivity to multiple scattering noise for HF receive signals obtained from a set of HF receive beams crossing the HF transmit beam at different depths along the HF transmit bam. When the multiple scattering noise is adequately low one can also obtain the NPDs from HF back-scatter receive signals from a HF receive beam with close to the same beam axis as the HF transmit beam, and gating the HF backscatter receive signal at different depths along the HF transmit beam.

To provide estimates of said parameters within a special estimation region (SER), the invention uses a mathematical model that from spatially varying parameters produces spatially varying model NPDs, and forms an estimation functional with a set of parameters as input forms a weighted sum of i) a distance function of the difference between the measured NPDs and said model NPDs for said set of parameters, weighted by a spatially variable distance weight, and ii) a gradient measure of the local variation of said parameter values within said SER, weighted by a spatially variable variation weight, and where local values of said distance weight and said variation weight are estimated from one or both of i) an assessment of local coherency of the HF receive signals, and ii) an assessment of the local magnitude of multiple scattered HF noise relative to the local magnitude of the first order scattered HF signal, and for a given set of measured NPDs, minimizing said EF with respect to said set of NEPs, and using the set of NEPs that minimizes said EF to form an estimate of spatially varying NEPs within said SER.

Said distance function and said gradient measure are based on functions $f(x)$ of the value x of the difference between said measurement outputs and said model outputs in each point of said SER, and where sign of the differential of $f(x)$ is equal to the sign of x. Said assessment of the local magnitude of multiple scattered HF noise relative to the local magnitude of the first order scattered HF signal is obtained from the measured NPDs that shows a drop in magnitude when multiple scattering noise in the HF receive signal increases, for example being below a fraction of an expected limit.

The minimization is typically done while enforcing local constrains on the parameters, such as a local maximal and minimal value. The distance weight can for example be formed as a ratio of a narrow region average to a larger region average (low-pass filter) of the envelope of the received HF signal for said local position, and said variation weight is formed as a positive function of said distance weight, where the differential of said positive function is negative.

An embodiment of the invention also provides synthetic lateral focusing of the HF receive range cells in said multitude of depths, through lateral filtering of the HF receive signals for multiple transmit beams using a set of filter coefficients, where said filter coefficients are determined analytically through one of i) pre-calculated filter coefficients, and ii) filter coefficients calculated from the estimated parameter values.

The measured NPDs can according to known methods be used for suppression of multiple scattering noise in the HF back-scatter receive signals, and also enhancement of non-linear scattering components in the HF receive signals, by correcting said HF back-scatter receive signals with said NPDs for each of said depths, and combining said corrected HF back-scatter receive signals.

An embodiment of the invention hence provides HF back-scatter receive signals with improved synthetic focusing and suppression of multiple scattering noise, in addition to estimates of the spatially varying material parameters.

An embodiment of the invention further provides instruments for transmitting at least two pulse complexes composed of co-propagating low frequency (LF) and high frequency (HF) pulses along at least one LF and HF transmit beam, where said HF pulse propagates close to the crest or trough of the LF pulse along at least one HF transmit beam, and where one of the amplitude and polarity of the LF pulse varies between at least two transmitted pulse complexes. Scattered HF pulse components are picked up by one or both of i) a HF backscatter receive beam with close to the same beam axis as the HF transmit beam, and ii) a set of HF receive cross-beams that crosses the HF transmit beam at a multitude of depths along the HF transmit beam axis. HF receive signals from a multitude of depths along the HF transmit beam axis are obtained by one or both i) gating the HF backscatter receive signal around said multitude of depths, and ii) gating the HF receive signals for said set of HF receive cross-beams around the crossing of the HF transmit beam at said multitude of depths.

A multichannel front-end unit provides HF and LF drive signals for a multi-element probe, and receiving HF element receive signals from said multi-element probe, and transferring said HF element receive signals to a HF receive beam-former that forms HF receive signals from a multitude of depths along the HF transmit beams, and transferring said HF receive signals to a measurement unit set up to compare HF receive signals for said multitude of depths from at least two different pulse complexes with differences in the LF pulse, to provide measured NPDs for said multitude of depths, and transferring said measured NPDs to an estimation unit that forms estimates of the spatially varying material parameters within said spatial estimation region as described above.

4. BRIEF DESCRIPTION OF THE DRAWINGS

5. DETAILED DESCRIPTION

5.1 Measurement Types Applicable to the Invention

Figure 1:
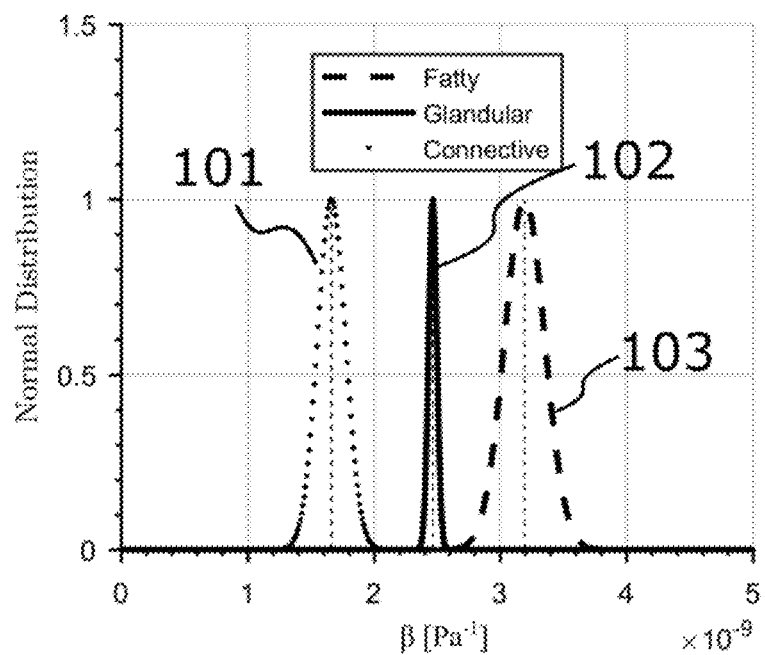
FIG. 1 shows prior art measured value distributions of the nonlinear elasticity parameter (NEP), β, for fatty, glandular, and connective tissues in female breasts.
Figure 2:
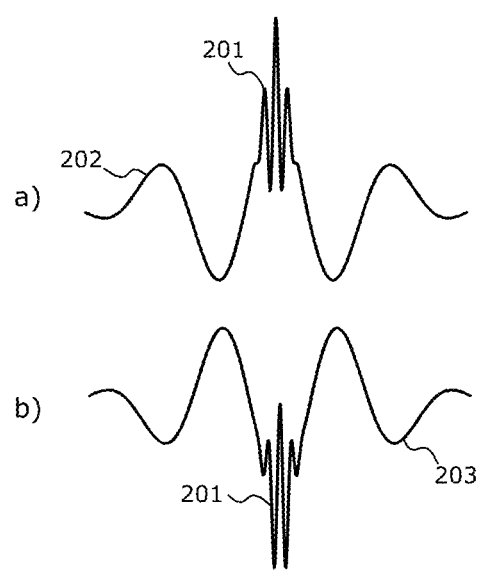
FIG. 2 shows prior art example pulse complexes comprising a high frequency (HF) pulse and a low frequency (LF) pulse, where two typical forms of LF pulses are shown.

The nonlinear elasticity parameter can be imaged with dual frequency ultrasound, where one for each beam direction transmits at least two dual band pulse complexes comprising overlapping high frequency (HF) and low frequency (LF) pulses. Two examples of such pulse complexes are shown in FIG. 2, where 201 shows the HF pulse and 202 shows the LF pulse. The HF:LF ratio is typically ~5:1-30:1. The LF pulse is used to nonlinearly manipulate the ultrasound scattering and propagation velocity observed by the HF pulse, and the scattered HF signal is processed to produce images. The LF pulse varies in amplitude and/or polarity between the transmitted pulse complexes. The LF pulse can be zero for one pulse complex, but must be non-zero for at least one pulse complex. FIG. 2a shows a LF pulse that is positive and compresses the material at the location of the HF pulse, so that the HF pulse observes an increased material stiffness with increased propagation velocity. FIG. 2b shows a change in polarity of the LF pulse so that the LF pulse is negative at the location of the HF pulse that expands the material and makes the HF pulse observe a softer material with lower propagation velocity.

Figure 3:
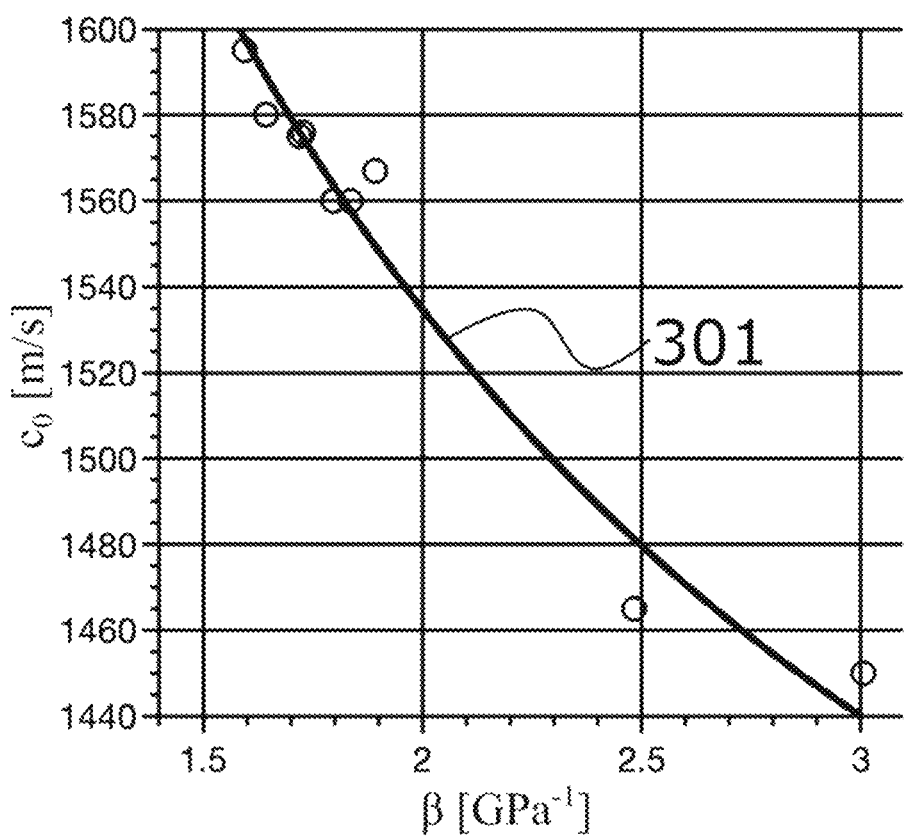
FIG. 3 shows the linear propagation velocity (m/s) as a function of nonlinear elasticity parameter ($10^{-9}$ $Pa^{-1}$).

FIG. 3 shows the values of c0 plotted against $\beta=\beta_n\kappa_s$ for the materials in Table I. The data are fitted by the curve 301

$$c_0(\beta) = \frac{1}{\sqrt{\kappa(\beta)\rho_0(\beta)}} \tag{3}$$

$$\kappa(\beta) = \frac{10^{-9}}{2a}\left[-b + \sqrt{b^2 + 4a\beta}\right]$$

$$\rho_0(\beta) = a_\rho \cdot \kappa(\beta) + b_\rho$$

$$a = 11.58$$

$$b = 0.023$$

$$a_\rho = -830 \cdot 10^9$$

$$b_\rho = 1371$$

This gives a suggestion that from the estimated value of $\hat{\beta}(\underline{r})$ in Eqs. (16, 21) we can estimate the spatially varying linear propagation velocity $c_0(\underline{r})$, which can be used for improved quality of the image reconstruction in many ways, which we return to below.

Figure 4:
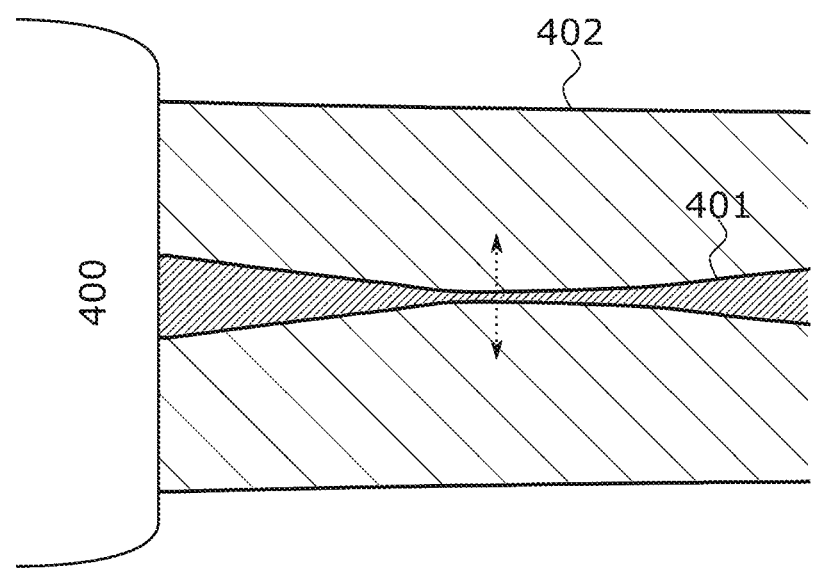
FIG. 4 is a schematic depiction of x-z cross section of the low frequency (LF) and high frequency (HF) transmit beams.

The HF and LF pulse complexes are transmitted along beams, where an example is shown in FIG. 4. Other examples are for example given in U.S. Pat. Nos. 8,038,616 and 9,291,493, and U.S. patent application Ser. No. 16/258, 251. Both the LF and the HF beams can be planar. What is important is that the HF and LF beams overlaps in a spatial measurement region (SMR) where the LF pulse nonlinearly manipulates the propagation velocity observed by the co-propagating HF pulse.

TABLE I

Material parameters used for FIG. 3, sorted by increasing
$\beta = \beta_n \kappa$ [11, 12]

| | Name | $\rho_0$ kg/m³ | $c_0$ m/s² | $\kappa^a$ GPa⁻¹ | $\beta_n$ | $\beta$ GPa⁻¹ |
|---|---|---|---|---|---|---|
| 1 | Liver | 1060 | 1595 | 0.371 | 4.3 | 1.59 |
| 2 | Muscle, skeletal | 1050 | 1580 | 0.382 | 4.3 | 1.64 |
| 3 | Non-fatty | 1055 | 1575 | 0.382 | 4.5 | 1.71 |
| 4 | Muscle, cardiac | 1060 | 1576 | 0.38 | 4.55 | 1.73 |
| 5 | Brain | 1040 | 1560 | 0.395 | 4.55 | 1.80 |
| 6 | Kidney | 1050 | 1560 | 0.391 | 4.7 | 1.84 |
| 7 | Spleen | 1054 | 1567 | 0.386 | 4.9 | 1.89 |
| 8 | Fatty | 985 | 1465 | 0.473 | 5.25 | 2.48 |
| 9 | Adipose | 950 | 1450 | 0.501 | 6 | 3.0 |

[a] Calculated as $\kappa = 1/\rho_0 c_0^2$.

The total transmitted pulse pressure in the SMR is hence $p(\underline{r},t)=p_L(\underline{r},t)+p_H(\underline{r},t)$, where $p_L$ is the LF and $p_H$ is the HF pulse. In accordance with Eq. (1) both $p_L$ and $p_H$ influences the propagation velocity observed by the HF pulse as $$c_H = c_0 + c_0 \beta p_L + c_0 \beta p_H \quad (4)$$

where $p_L$ is the LF pressure at the center of the HF pulse. The last term produces a self-distortion of the HF pulse that gives harmonic frequency bands of the HF pulse used in current harmonic imaging. For the $2^{nd}$ term $p_L$, varies so slowly along the HF pulse that the effect of this term on the HF pulse can be divided into two phenomena: i) a nonlinear propagation delay (NPD) produced by the value of $p_L=p_c$ at the center of gravity of the HF pulse, and ii) a nonlinear pulse form distortion (PFD) produced by the variation of $p_L$, along the HF pulse.

Due to the LF manipulation of the HF propagation velocity, the HF pulse obtains a propagation time delay to a depth z as $$t(\underline{r}) = \quad (5)$$

$$\int_{\Gamma(\underline{r})} \frac{ds}{c(s, p_c(s))} \approx \int_{\Gamma(\underline{r})} \frac{ds}{c_0(s)} - \int_{\Gamma(\underline{r})} \frac{ds}{c_0(s)} \beta(s) p_c(s) = t_0(\underline{r}) + \tau_p(\underline{r})$$

$$t_0(\underline{r}) = \int_{\Gamma(\underline{r})} \frac{ds}{c_0(s)}$$

$$\tau_p(\underline{r}) = -p \int_{\Gamma(\underline{r})} \frac{ds}{c_0(s)} \beta(s) p_c(s)$$

where $\tau_\square(z)$ is the nonlinear propagation delay (NPD) and $\Gamma(\underline{r})$ is the transmit beam axis. The last formula indicates that $\beta(\underline{r})$ can be obtained from differentiation of $\tau_p(\underline{r})$, but due to noise in the measured $\tau_p(\underline{r})$, direct differentiation produces very noisy estimates of $\beta(\underline{r})$, where the invention presents solutions to this problem.

For objects that allow through transmission of pulse complexes along beams, like the breast and the testicles, one can measure $\tau_p$ from the difference in arrival time of the first HF pulse from two transmitted pulse complexes with different LF pulses, for example a positive LF pulse (p=1) and a zero LF pulse (p=0), or a positive LF pulse (p=1) and a negative LF pulse (p=−1). Lateral scanning the through transmit beams with different directions so that each measurement volume is traversed by beams in 180 deg of directions, one can do tomographic reconstruction of $\beta(\underline{r})$ according to known methods described in [15]-[19].

However, for most medical objects one must rely on scatter measurements with a limited angle between the transmit and receive beams, for example direct back scattering or angular scattering using crossing transmit and receive beams, as described. On can then make use of the approximation that at the first scattering, the amplitude of the LF pulse drops so much that one can neglect the nonlinear effect of the LF pulse on the propagation velocity of the scattered HF pulse.

Figure 5:
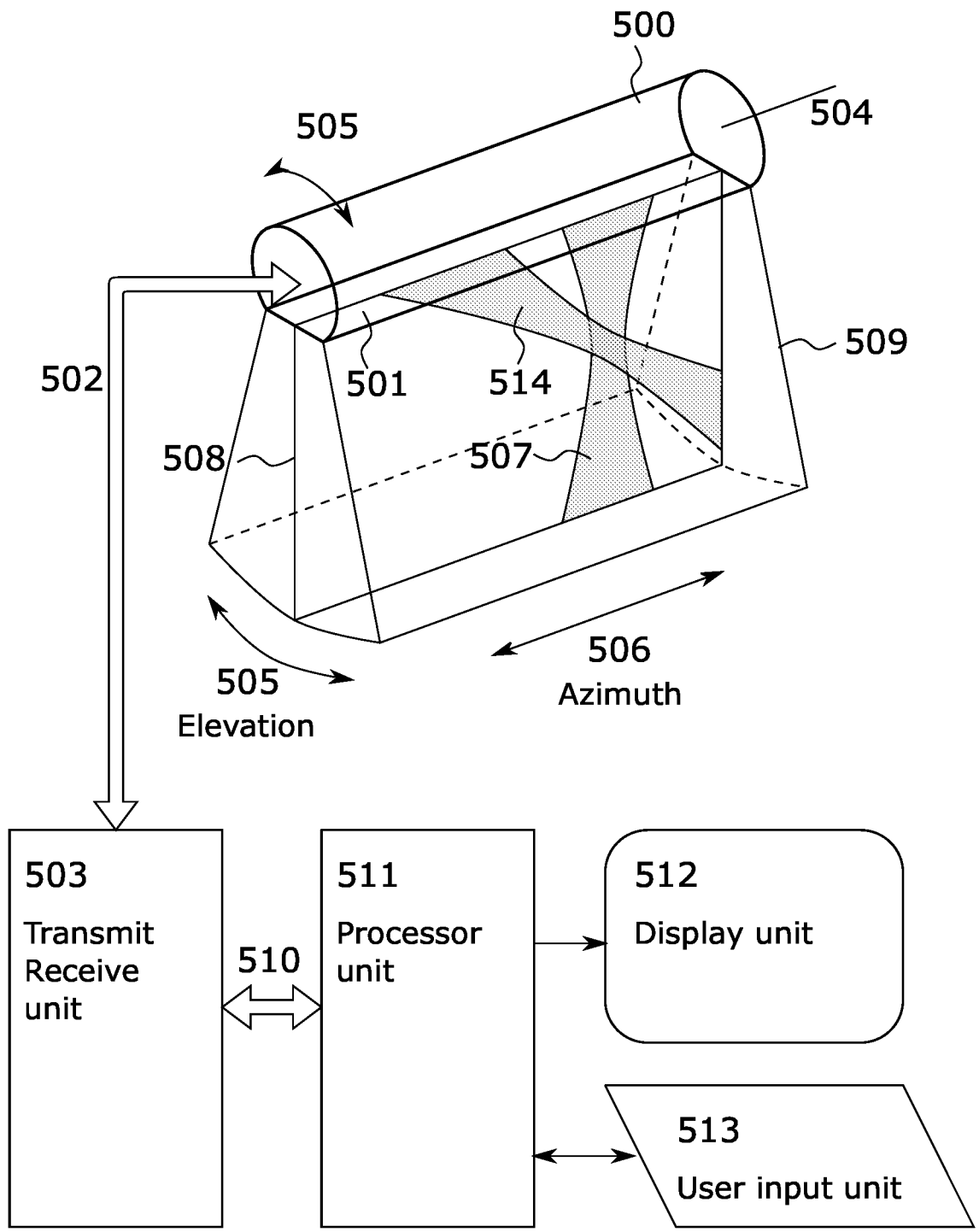
FIG. 5 is a block diagram of ultrasound instrument according to the invention

For better reference to describe the methods of embodiment of the invention, we show in FIG. 5 a block diagram of an example instrument for carrying out imaging according to the invention. 500 shows by example a 3D ultrasound probe comprising a dual frequency linear array 501 with a set of M LF elements and N HF elements in an azimuth direction indicated by the arrows 506. The dual frequency band linear array can be made according to known methods, for example as described in [5] U.S. Pat. No. 7,727,156. The LF and HF elements of the array are via a cable 502 connected to a transmit/receive unit 503 that connects each LF array element to LF transmit amplifiers, and each HF element to HF transmit/receive circuits comprising a HF transmit amplifier and a HF receive amplifier where the output of the HF receive amplifier is further connected to an analog to digital converter (A/D) presenting a digital representation of the HF received signals from all HF receive elements, according to known methods. The AD converter can in a modified embodiment present digital representations of the I-Q components of the HF receive signals from each HF element that represents the same information as the radio frequency (RF) HF signal, according to known methods.

For 3D scanning of the ultrasound beams, the linear array 501 can in this example embodiment be rotated around the long axis 504 that provides a mechanical scanning of the LF/HF beam in an elevation direction, indicated by the arrows 505. For each elevation position of the array, one does electronic scanning of a combined LF/HF transmit beam in an azimuth direction indicated by the arrows 506, through electronic selection of transmitting LF and HF elements, and transmitting combined LF/HF pulse complexes similar to what is shown in FIG. 2, with selected beam directions and focus. An example HF transmit beam is illustrated schematically as 507 within a 2D azimuth plane 508 with given elevation position within a total 3D scan volume 509. Alternative elevation movements of the array, like side-ways movement can equivalently be done according to known methods, depending on the space available for such movement, and the shape of the object. Pure 2D scanning of the beam, and even measurements along a single beam direction is also within the scope of the invention.

At least two pulse complexes with different LF pulses, for example as illustrated in FIG. 2, are transmitted for each transmit beam direction. The LF pulse might be zero in one pulse complex per HF transmit beam, but must be non/zero in at least one pulse complex for each HF transmit beam.

Two versions of the instrument are useful, where in the first version 503 comprises beam former for HF receive cross-beams, illustrated as 514 in the 2D scan plane 508, and HF back scatter receive beams with the same axis as the HF transmit beam 507. In a preferred embodiment the HF back-scatter receive beam is equal to the HF transmit beam as this improves suppression of multiple scattering noise in the HF back-scatter receive signal, as discussed in U.S. Pat. No. 9,291,493, and synthetic depth optimized focus is obtained through lateral filtering of the HF receive signals. During the scan, the HF cross-beam and back-scatter receive signals are via the high speed bus 510 transferred to the processor 511 for storage and further processing.

The processor 511 comprises a multicore central processing unit (CPU) and a graphics processor unit (GPU) that are SW programmable. The processor receives user inputs from a user/operator input unit 513 that operates according to known methods, and displays image data and other information necessary for communication with the user/operator through a combined display and audio unit 512, according to known methods.

In the second version, the digital HF receive signals from each HF receive elements and each transmitted pulse complex are via the high-speed bus 510 transferred to the processor 511 for storage and further processing. For 2D imaging in the second version, a SW program in the processor 511 combines HF receive signals from multiple HF receive elements and produces a set of HF receive cross-beams crossing each HF transmit beam in the 2D set, for example as shown in more detail in FIG. 5 below. A SW program also produces a set of HF back-scatter receive signals from HF back-scatter receive beams with the same axis as the HF transmit beams, and preferably also equal to the HF transmit beams.

The main use of the cross-beams HF receive signals is to estimate the nonlinear propagation delay at a multitude of depths along the HF transmit beam. When we have imaging situations where the level of multiple scattering noise in the back-scatter HF receive signal is low compared to the 1st order scattered signals, the nonlinear propagation delay at multitude of depths along the HF transmit beam can be obtained from the back-scatter HF receive signal, and the beam former for HF receive cross-beams, has less importance and can be omitted.

Figure 6:
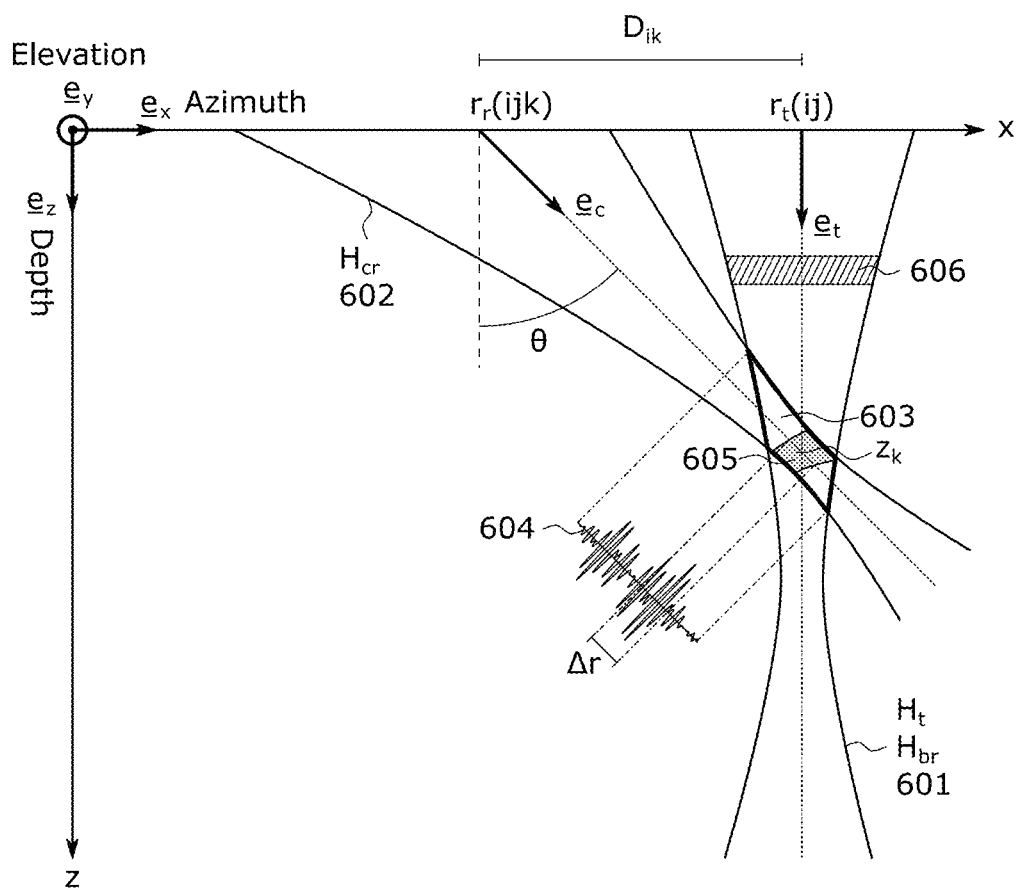
FIG. 6 shows typical positioning of HF receive cross-beam in relation to HF transmit and back-scatter receive beams.

Example HF transmit and receive beams are shown in FIG. 6, where 601 shows by example a combined HF transmit beam, $H_t$, and equal HF back-scatter receive beam, $H_{br}$. The spatial frequency responses of the HF transmit beam and the HF back-scatter receive beam are $H_t(\underline{r}-\underline{r}_t,\omega)$ and $H_{br}(\underline{r}-\underline{r}_t,\omega)$. The position vector $\underline{r}_t(i,j)$ defines the origin of the HF transmit and backscatter receive beam axes, where i defines the azimuth aperture center element position, and j defines the 2D scan plane elevation position in a 3D scan. 602 shows an example HF receive cross-beam focused at the HF transmit beam axis at depth $z_k$, $H_{cr}(\underline{r}-\underline{r}_r,\omega)$, where $\underline{r}_r(i,j,k)$ defines the origin of the HF receive cross-beam axes, where i,j defines the azimuth and elevation position, and k defines the depth of the cross-over image point $z_k$ that is also the focus point of $H_{cr}$. 603 shows a cross-beam observation cell by the cross-over region between a HF transmit beam and the HF receive cross-beam, and 604 shows an indication of a HF cross beam receive signal from the whole cross-over region. By selecting a limited interval of this HF receive signal, the effective range of the observation cell is reduced along the cross-beam axis to the hatched region 605. A schematic form of the HF back-scatter observation cell is shown as the hatched region 606, along the HF combined transmit and back-scatter receive beams 601. The dimensions of the observation cells can be reduced by spatial filtering of the HF receive signals, as shown in U.S. Pat. No. 9,291,493 and U.S. patent application Ser. No. 16/258,251.

For special versions of the processing one might also use all LF/HF array elements to transmit LF/HF beams that are approximately plane in the azimuth direction. Transmitting azimuth plane waves in several directions one can combine the received signals from the different directions to produce synthetic transmit beams focused at different locations within the 2D plane, according to known methods [4]. With a single azimuth direction plane wave, one can obtain spatial resolution with regular back-scatter registration of several parallel, dynamically focused receive beams, where time of arrival of scattered pulses produces spatial resolution along the depth of each receive beam, while the receive beam focusing produces lateral spatial resolution, all according to known methods. This method is however more sensitive to multiple scattering noise than the cross beam method described.

Estimates of the NPD can for low level of multiple scattering noise in relation to the level of the 1st order back scattered signal, be obtained directly from the back scattered HF signal at multiple depths z along the transmit beam. Such a situation often occur with endoscopic probes. It is then sufficient to only use the HF back-scatter receive beam, $H_{br}$, shown as 601 in FIG. 6, for reception. This allows a simpler instrument for such applications. With higher levels of multiple scattering noise, typically found in transcutaneous imaging, it is an advantage to also use HF cross-beam signals obtained with the receive HF cross-beam, shown as 602 in FIG. 6. This requires an added receive HF cross-beam former, which can be implemented in software in the second version of beam-forming described above.

Estimates of the NPD can then be obtained from the HF receive signals at several observation cells along each transmit beam direction, for example through i) cross correlation between the HF receive signals from pulse complexes with a positive LF pulse and a zero LF pulse, giving $\tau_+$ that is negative according to Eq. (5), or ii) cross correlation between the HF receive signals from pulse complexes with a negative LF pulse and a zero LF pulse, giving $\tau_-$ that is positive according to Eq. (5), and iii) cross correlation between the HF receive signals from pulse complexes with a positive LF pulse and a negative LF pulse, giving approximately $2\tau_+$ according to Eq. (5). The term approximately arises from that the LF wave-front can produce some HF wave front aberration. This HF wave aberration is somewhat different for the positive and negative LF pulses.

The received signal from an observation cell arises from interference between signals from random scatterers, that produces noise in the correlation estimates of the NPD. This interference varies with the direction of the HF receive beam in relation to the HF transmit beam. Averaging of the estimated NPDs from HF receive beams with different directions can then be used to reduce estimates in the NPD for each depth along the HF transmit beam. With low level of multiple scattering noise, one can also combine estimates from back-scatter and cross-beam HF receive signals.

This procedure gives a noisy measurement of the NPD along a transmit beam axis $\Gamma(\underline{r})$ defined by the vector $\underline{r}(\underline{r}_t,z)=\underline{r}_t+z\underline{e}_t$, where $\underline{r}_t$ defines an origin of the transmit beam axis, $\underline{e}_t$ is the unit vector along the transmit beam axis, and z is the distance along the transmit beam axis from its origin $\underline{r}_t$, as shown in FIG. 6. From Eq. (5) we describe the noisy NPD measurement, $\tau_y(\underline{r}_t,z)$, as $$\tau_y(\underline{r}_t,z) = \hat{\tau}(\underline{r}_t,z;\beta) + n(\underline{r}_t,z) \qquad (6)$$

$$\hat{\tau}(\underline{r}_t,z;\beta) = -p\int_0^z \frac{ds}{c_0(s)}\beta(\underline{r}_t,s)p_{Lc}(\underline{r}_t,s)$$

where $\hat{\tau}(\underline{r}_t,z;\beta)$ is the model of the NPDs for given values of the nonlinear elasticity parameter (NEP), $\beta(\underline{r}_t,z)$, given in Eq. (5), and $n(\underline{r}_t,z)$ is a noise term that occurs both from the method of delay estimation, and from noise in the HF receive signals used for the delay estimation.

Figure 7:
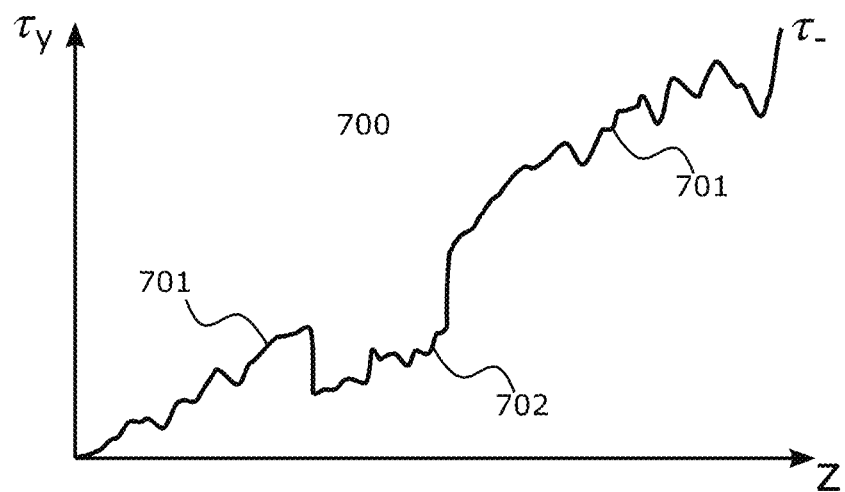
FIG. 7 shows typical measured nonlinear propagation delay (NPD) as a function of depth z.

A typical form of $\tau_y(\underline{r}_t,z)$ is given as 700 in FIG. 7. When the HF receive signal is dominated by 1st order scattered signal from a depth r plus random electronic noise, the noise $n(\underline{r}_t,z)$ oscillates around $\tau_y(\underline{r}_t,z)$ with close to zero average value. This situation is shown as 701. As $\beta(\underline{r})>0$, $\hat{\tau}(\underline{r}_t,z;\beta)$ has a differential with depth given by (−p), and $\tau_y(\underline{r}_t,z)$ has an oscillatory behavior around this $\hat{\tau}(\underline{r}_t,z;\beta)$. From cysts and vessels, for example, the 1st order scattered HF signal is low, and the received signal can then be dominated by multiple scattering noise, referred to as reverberations, typically 3rd order multiple scattering noise which has a nonlinear propagation delay, $\tau_n(\underline{r})\sim\tau_y(\underline{r})/2$, as shown in U.S. Pat. No. 9,291, 493. The measured NPD $\tau_y(\underline{r}_t,z)$ in a region where 3rd order scattering noise dominates the HF receive signal, hence produces a drop in $\tau_y(\underline{r}_t,z)$ shown as 702. $\tau_y(\underline{r}_t,z)$ is not useful for estimation of $\beta(\underline{r})$ in this region, and the estimation procedure according to the invention presents solutions to this problem.

Due to a high noise/signal ratio in the measurement of $\tau_y(\underline{r}_t,z)$, direct differentiation of $\tau_y(\underline{r}_t,z)$ with z produces a very noisy estimate of $\beta(\underline{r}_t,z)$ with also a potential noisy non-zero offset in the differential $\partial n(\underline{r}_t,z)/\partial z$ for regions dominated by reverberations. The challenge is hence to provide an adequate estimate of $\beta(\underline{r}_t,z)$ with adequate low noise/uncertainty, and the invention devises a robust method of estimating the nonlinear elasticity parameter (NEP), $\beta(\underline{r}_t,z)$, for $(\underline{r}_t,z)$ in a spatial estimation region (SER) from the measured nonlinear propagation delay (NPD), $\tau_y(\underline{r}_t,z)$, for $(\underline{r}_t,z)$ in a spatial measurement region (SMR).

Figure 8:
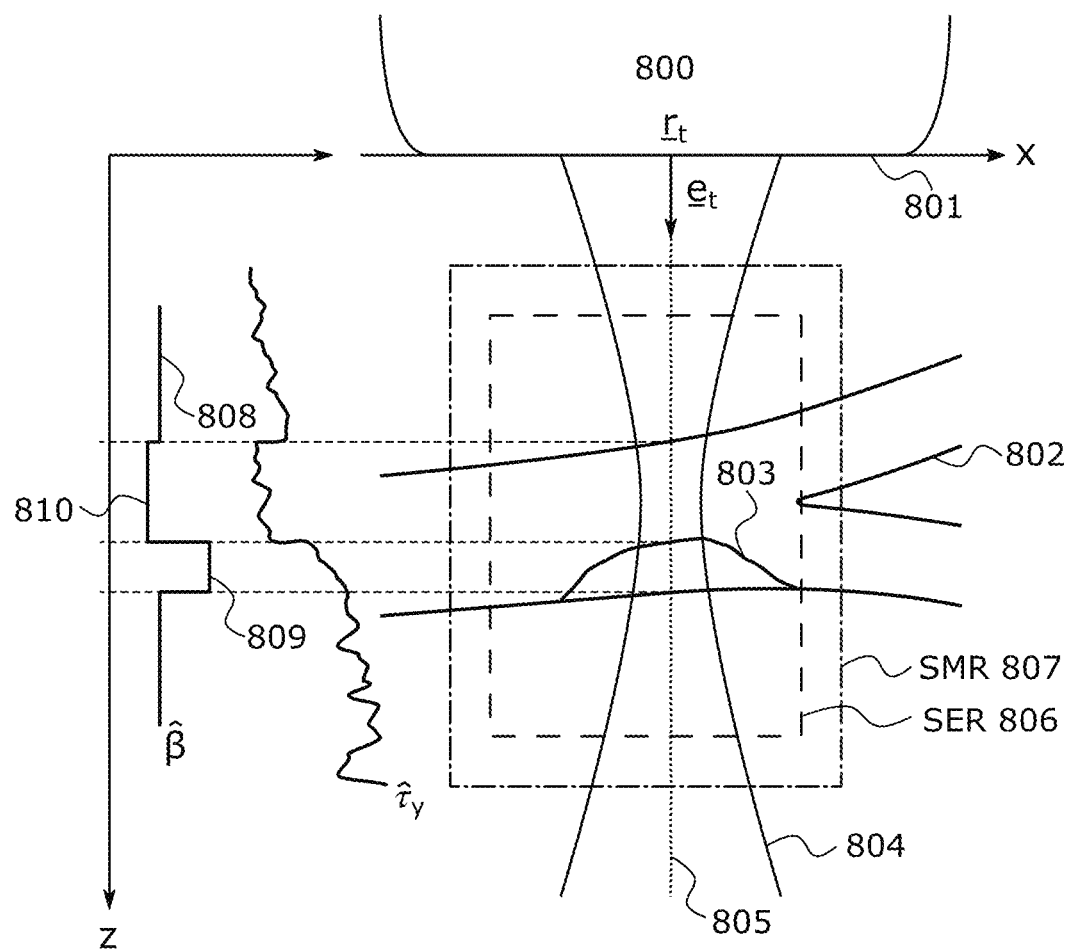
FIG. 8 shows example image format with example transmit beam originating at lateral vector position $\underline{r}_t$, depth coordinate z, and direction unit vector $\underline{e}_t$, spatial measurement region (SMR) and spatial estimation region (DER).

FIG. 8 gives an example illustration of the measurement situation where 800 shows a linear array at the surface of a tissue region 801 comprising a bifurcating artery 802 with an atherosclerotic plaque 803. 804 shows a HF transmit beam with axis 805 originating at the location $\underline{r}_t$, defining a point on the beam axis $\Gamma(\underline{r})$ at depth z as $\underline{r}(\underline{r}_t,z)=\underline{r}_t+z\underline{e}_t$. A typical example of SER and SMR are shown as 806 and 807. 701 illustrate the measured NPD $\tau_y(\underline{r}_t,z)$, similar to the one shown in FIG. 7. Estimated values $\hat{\beta}$ are shown as 808, where within the plaque one obtains a specially high $\hat{\beta}$ value 809, while 810 shows a low $\hat{\beta}$ inside the blood region of the artery.

The HF receive signal within the artery is dominated by multiple scattering noise giving a reduced $\tau_y$ per the discussion regarding FIG. 7, where the estimation according to the invention presents an estimate for the homogeneous blood region by comparing the value of r before entering the noise dominated signal from the blood where $\tau_y$ drops in value, to the value of $\tau_y$ when leaving this region where $\tau_y$ reaches the high value where the HF receive signal is dominated by 1st order scattering, as discussed below. The forward propagation through the blood region has the propagation velocity and NEP of the blood, hence, $\hat{\tau}(\underline{r}_t,z;\beta)$ develops according to Eq. (6), while $\tau_y(\underline{r}_t,z)$ obtained from the HF scattered signal is dominated by the multiple scattering noise in the blood region. However, when z enters the strongly scattering plaque, the 1st order scattering restarts to dominate the HF receive signal, and $\tau_y(\underline{r}_t,z)$ again reflects $\hat{\tau}(\underline{r}_t,z;\beta)$. Comparing $\tau_y(\underline{r}_t,z)$ just before z enters the artery to $\tau_y(\underline{r}_t,z)$ just after z has left the artery allows us to estimate $\hat{\beta}$ for the blood inside the artery, for example using the ideas of W=0 as discussed below. Due to the high value of $\beta$ in the plaque, $\tau_y$ has an increased derivative within the plaque, before leveling off to a derivative for the tissue around the artery.

5.2 Estimation of the Nonlinear Elasticity Parameter

A central part of the method is minimization of an estimation functional (EF) with respect to $\beta(\underline{r})$ and other parameters. The estimation functional (EF) is a weighted combination of i) a distance function $F_\tau(\cdot)$ of the difference between said measured NPDs, $\tau_y(\underline{r}(\underline{r}_t,z))$, and the model NPDs, $\hat{\tau}(\underline{r}_t,z;\beta)$, for a given set of NEP estimates in said SERs, where both $\tau_y$ and $\hat{\tau}$ are given in Eq. (6), and ii) a measure function, $F_g(\cdot)$, of the local variation of said NEP estimates around said SERs.

An example of such an estimation functional is $$H\{\beta(\underline{r}_t,z)\} = \int_{R_t} dr_{t0} \qquad (7)$$

$$\int_Z dz\{W(\underline{r}_{t0},z)F_d[\tau_y(\underline{r}_{t0}z;\beta(\underline{r}_{t0},z))] + V(\underline{r}_{t0},z)F_g[\nabla\beta(\underline{r}_{t0},z)]\}$$

Subject to constraints: $\beta_{min}<\beta(\underline{r}_t,z)<\beta_{max}$

The distance and the measure functions satisfies the following requirements and examples $$F_k(0) = 0 \qquad (8)$$
$$\text{sign}\left\{\frac{\partial F_k(x)}{\partial x}\right\} = \text{sign}\{x\}$$
$$k = d, g$$

with typical forms of $F_k$ as $$F_k(x) = |x|^p \text{ or } F_k(x) = \begin{cases} |x|^{p_1} & \text{for } |x| \leq x_1 \\ |x_1|^{p_1} + (|x|-|x_1|)^{p_2} & \text{for } |x| > x_1 \end{cases} \qquad (9)$$

Figure 9:
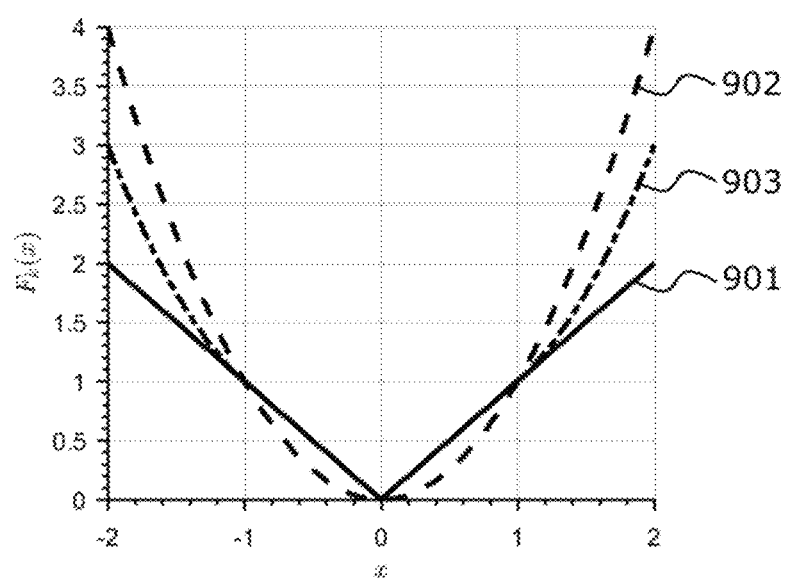
FIG. 9 shows example distance and measure functions.

Examples of distance and measure functions are given in FIG. 9, where 901 shows $F_k(x)=|x|$, i.e. p=1, 902 shows $F_k(x)=|x|^2$, i.e. p=2, and 903 shows the last form of $F_k(x)$ where $x_1=1$, $p_1=1$ and $p_2=2$.

$W(\underline{r}_t,z)$ is a spatial distance weighting term that manages penalty for deviation of the model NPD, $\hat{\tau}$, from the measured NPD, $\tau_y$, while $V(\underline{r}_t,z)$ is a spatial variation weighting term that manages penalty for rapid variations in the NEP estimate $\beta(\underline{r}_t,z)$. A reduction in $V(\underline{r}_t,z)$ relaxes smoothness requirements, for example in a region where a large gradient in the NEP estimate is expected, for example at a fairly plane interface between two materials that gives a strong reflection. At such a fairly plain interface between materials with different acoustic impedance, the reflected SNR is high, and we expect $\tau_y(\underline{r}_t,z)\approx\hat{\tau}(\underline{r}_t,z)$. At such locations we want W≈1 and V≈0, as we are likely close to a transition into a new material with a change in the NEP estimate $\beta$. In contrast, if a region has highly incoherent HF receive signal, we expect the SNR to be lower and can consequently relax the penalty for deviation, i.e. W moves towards 0, while V moves towards a high value η so that $V \cdot F_g[\nabla\beta]$ becomes dominant in H, suppressing rapid variations in the NEP estimate $\beta$.

These weights can be applied in both the lateral and the axial beam directions. The role of W is to detect strong scatterers, e.g., specular reflections, typically originating from the interface between two materials. Useful formulas are a) $W(\underline{r}_t, z) = \dfrac{h_{T\lambda} \underset{z}{\otimes} e_0(\underline{r}_t, z)}{h_{T3\lambda} \underset{z}{\otimes} e_0(\underline{r}_t, z)}$ (10)

b) $V(\underline{r}_t, z) = \eta[1 - W(\underline{r}_t, z)]$ where $e_0(\underline{r}_t, z)$ is the envelope of the received RF data for a zero LF transmission (p=0), and $h_{T\lambda}$, and $h_{T3\lambda}$ are impulse responses of averaging low pass filters for one and three wavelengths, respectively. The ratio of these two low-pass filtered versions of the envelope, acts as a high-pass filter, identifying regions where the local scattering deviates from the surrounding diffusive scattering. The weighting factor is normalized for each transmission, scaling the maximum value along each receive line to $W_{max}=1$. $V(\underline{r}_t, z)$ is then in this experiment obtained from Eq. (10b) where the weighting factor $\eta$ is adjusted by the operator for best performance. An embodiment also presents a method for computer adapted adjustment of $\eta$ using machine learning techniques.

An embodiment also presents the use of the measured $\tau_y(\underline{r}_t, z)$ in the assessment of the functional weights $W(\underline{r}_t, z)$ and $V(\underline{r}_t, z)$. An unexpected slow increase in $\tau_y(\underline{r}_t, z)$ can be used to reduce $W(\underline{r}_t, z)$ while increasing $V(\underline{r}_t, z)$ for example according to Eq 9b. Regions $\Omega$ where the HF receive signal is dominated by multiple scattering noise, as from inside a cyst or a vessel, can be detected by an unexpected drop in $\tau_y(\underline{r}_t, z)$ with z, as demonstrated in FIG. 7, 8. Hence, if $\tau_y(\underline{r}_t, z) < k \cdot L_z\{\tau_y(\underline{r}_t, z/2)\}$, where $L_z$ is a short low-pass filter, e.g. a median filter, and $k \sim 1.5$ is a parameter, we set $W(\underline{r}_t, z)=0$.

Figure 10:
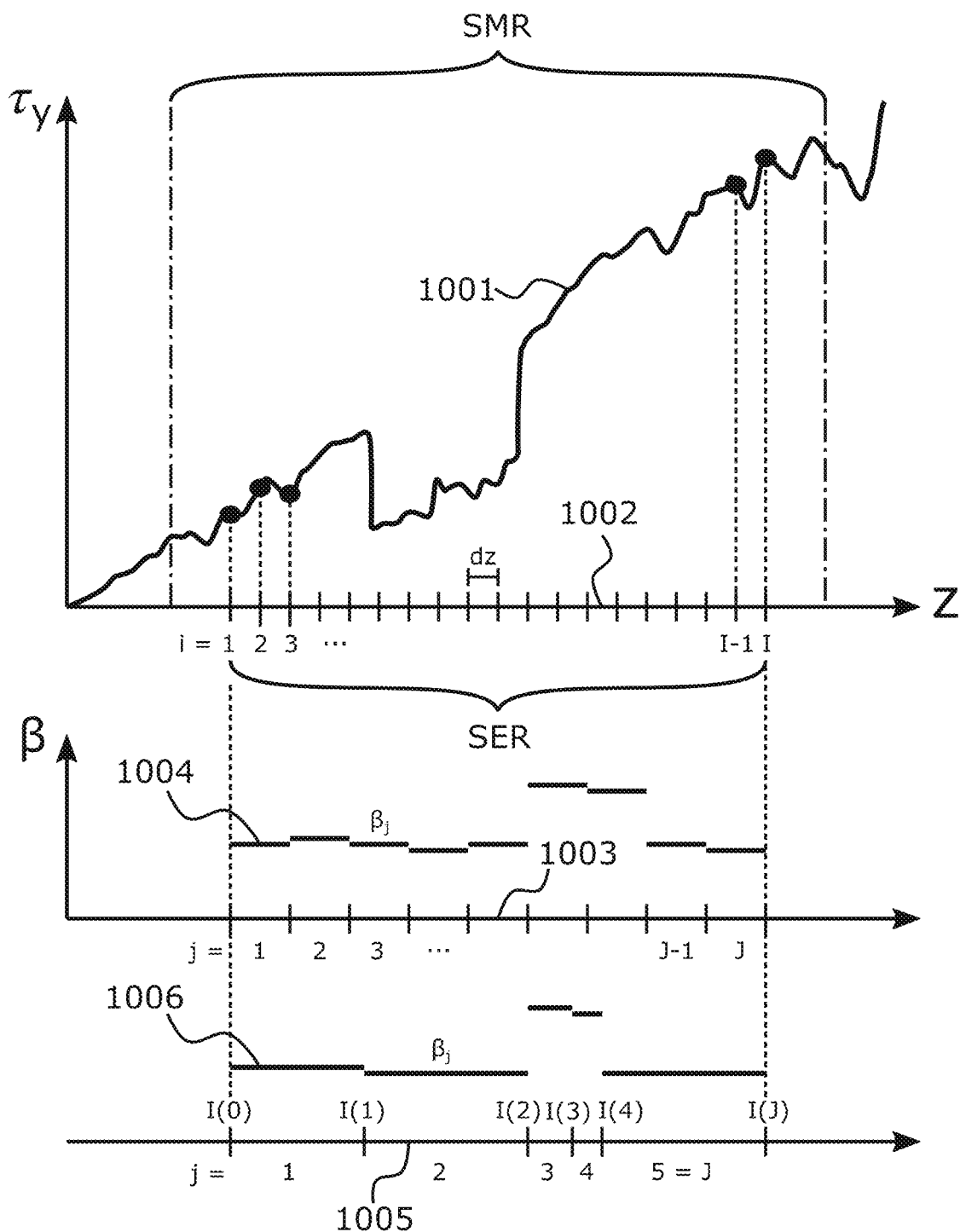
FIG. 10 shows sample division of the nonlinear propagation delay (NPD), $\tau_i$, and sample division for the nonlinear elasticity parameter (NEP), $\beta_j$, with fixed sample intervals 1003, and sample intervals with variable length 1005.
Figure 11:
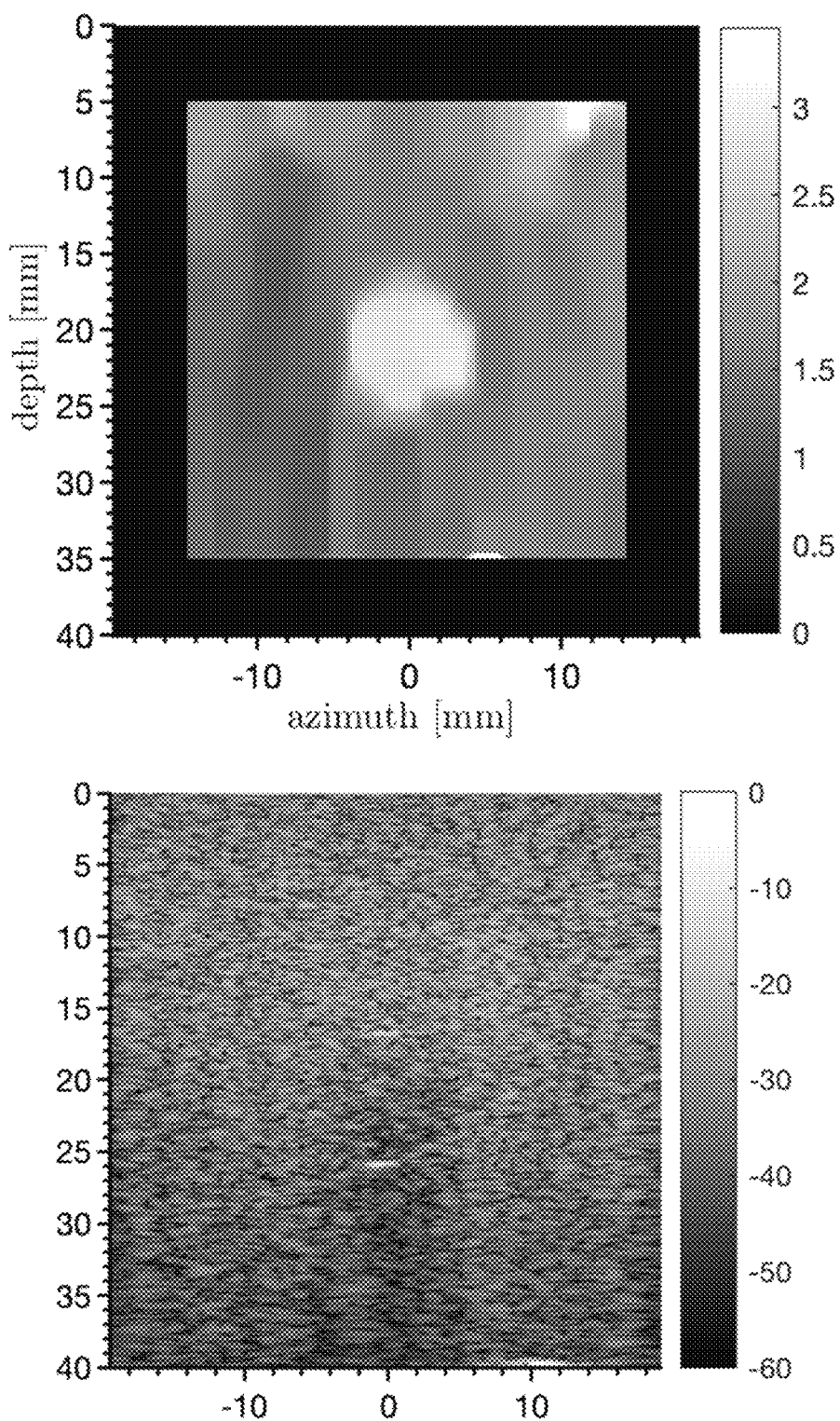
FIG. 11 shows in a) a regular ultrasound image of a phantom with a fatty lump in the middle with the same scattering characteristics as the surrounding material, and in b) is shown the image of the spatially varying nonlinear elasticity parameter $\hat{\beta}(\underline{r})$ obtained according to the invention.

In FIG. 10, 1001 shows how the measured NPD, $\tau_y(\underline{r}_t, z)$, is sampled in a discrete set of intervals $i \cdot dz$ for an interval Z along the transmit beam, as shown, where $i=1, 2, \ldots, I$, shown as 1002. The measured NPDs are then represented by the vector of dimension I $$\underline{\tau} = \{\tau_1, \tau_2, \ldots, \tau_i, \ldots, \tau_I\} = \{\tau_y(z_0 + idz) \text{ for } i=1, \ldots I\} \quad (11)$$

We typically have $dz \sim \lambda_H/4 - \lambda_H$, where $\lambda_H$ is the HF wavelength, and the number of measurement points for the NPD is typically $I \sim 256-1024$.

In one variant of the procedures, the interval Z is further divided into J subintervals of equal length and labeled $j=1, 2, \ldots, J$, shown as 1003, where we assume the NEP parameter $\beta_j$ is constant along each sub interval, illustrated as 1004. The minimal length of sub-intervals is typically given by the measurement resolution along the axis of the transmit beam which is typically of the order of the HF pulse length $\sim 3-4\lambda_H$, which implies that $J \sim 64-256$. In each sub-interval we seek a constant estimate $\beta_j$, $j=1, 2, \ldots, J$, of the nonlinear elasticity parameter NEP in each interval. The end-point of each j-interval in i-coordinate numbers is $I(j)=j \cdot I/J$, with the starting point $I(0)=0$. The NPD model within each interval #j is hence give as $$\hat{\tau}_i(\underline{\beta}) = \hat{\tau}_{I(j-1)} + \beta_j[i - I(j-1)]dz/c_0$$

$I(j-1) < i \leq I(j)$ for $j=1, \ldots, J$  $I(0)=1$  $I(J)=I$ (12)

and we define the parameter vector as $$\underline{a} = \{a_k\} = \{\beta_1, \beta_2, \ldots, \beta_J\}\ k=1,2,\ldots,K\ K=J \quad (13)$$

For the gradient of $\beta$ defined versus z in Eq. (7), we can for example assume a linear interpolation to the coordinate #i between the values located near the center of the j-th interval. We can hence represent the gradient by the vector function $\underline{G}(\underline{a})$.

In another variant of the procedures we use variable length of the J sub-intervals for each NEP parameter along the transmit beam, and we want to vary both the sub-interval connection points and the NEP parameters $\beta_j$ for each sub-interval, to find the best adaptation of the model $\hat{\underline{\tau}}$ to the measurements $\tau_y$. A schematic example is shown as 1005 where the total sample interval for NPD measurements, $\tau_y$, is in the interval $I_Z$ $$i \in I_Z \Rightarrow I_Z = \{1, \ldots, I\} = \{1 - I(1); I(1) - I(2); \ldots; I(j-1) - I(j); \ldots; I(J-1) - I\} \quad (14)$$

We then define a total parameter vector as $$\underline{a} = \{a_k\} = \{\beta_1, \beta_2, \ldots, \beta_J, I(1), I(2), \ldots, I(J-1)\} \quad (15)$$

i.e. a total of $K=2J-1$ parameters. We define $\underline{G}(\underline{a})$ as the gradient of primarily the $\beta$ part of $\underline{a}$, but potentially also including the connection points $I(j), j=1, 2, \ldots, J-1$ in the gradient term. Eqs. (7, 8) then transforms to $$H(\underline{a}) = \sum_{i=1}^{I} \{W_i F_d[\tau_i - \hat{\tau}_i(\underline{a})] + V_i F_g[G_i(\underline{a})]\} \quad (16)$$

Evaluating $H(\underline{a}+\underline{h})$ to the 2nd order in $\underline{h}$ gives $$H(\underline{a}+\underline{h}) \approx H(\underline{a}) + \left(\dfrac{\partial H(\underline{a})}{\partial \underline{a}}\right)^T \underline{h} + \dfrac{1}{2}\underline{h}^T \dfrac{\partial^2 H(\underline{a})}{\partial \underline{a} \partial \underline{a}} \underline{h} \quad (17)$$

$$\dfrac{\partial H(\underline{a})}{\partial \underline{a}} = \left(\dfrac{\partial H(\underline{a})}{\partial a_k}\right)$$

$$\dfrac{\partial^2 H(\underline{a})}{\partial \underline{a} \partial \underline{a}} = \left(\dfrac{\partial^2 H(\underline{a})}{\partial a_k \partial a_l}\right)$$

where the 1st derivative is a vector and the 2nd derivative is a matrix. The details of the differentiation gives $$\dfrac{\partial H(\underline{a})}{\partial a_k} = \sum_{i=1}^{I} \left\{ W_i F_d'[\tau - \hat{\tau}_i(\underline{a})]\dfrac{\partial \hat{\tau}_i}{\partial a_k} + V_i F_g'[G_i(\underline{a})]\dfrac{\partial G_i}{\partial a_k} \right\} \quad (18)$$

$$\dfrac{\partial^2 H(\underline{a})}{\partial a_k \partial a_l} =$$

$$\sum_{i=1}^{I} \left\{ W_i F_d'[\tau_i - \hat{\tau}_i(\underline{a})]\dfrac{\partial^2 \hat{\tau}_i}{\partial a_k \partial a_l} + W_i F_d''[\tau_i - \hat{\tau}_i(\underline{a})]\dfrac{\partial G_i}{\partial a_k}\dfrac{\partial G_i}{\partial a_l} + V_i F_g'[G_i(\underline{a})]\dfrac{\partial^2 \hat{\tau}_i}{\partial a_k \partial a_l} + V_i F_g''[G_i(\underline{a})]\dfrac{\partial G_i}{\partial a_k}\dfrac{\partial G_i}{\partial a_l} \right\}$$

The differentials can be obtained both numerically and analytically. Differentiation the above approximation of $H(\underline{a}+\underline{h})$ with respect to $\underline{h}$ and equating to zero gives $$\dfrac{\partial H(\underline{a})}{\partial \underline{a}} + \dfrac{\partial^2 H(\underline{a})}{\partial \underline{a} \partial \underline{a}} \underline{h} = 0 \quad (19)$$

and equating to zero gives the well-known Newton-Raphson iteration procedure $$a_{n+1} = a_n + h(a_n) \quad (20)$$

$$h(\underline{a}) = -\left(\frac{\partial^2 H(\underline{a})}{\partial \underline{a} \partial \underline{a}}\right)^{-1} \frac{\partial H(\underline{a})}{\partial \underline{a}}$$

Subject to constraints: $\beta^{min} < \alpha_{n+1,j} < \beta_{max}$ j=1,2, . . . ,J Observability of the parameters is determined by invertability of the 2nd order derivative matrix $\partial^2 H(\underline{a})/\partial \underline{a} \partial \underline{a}$.

Using $L^2$ norms for the distance and gradient measures by example, i.e. $F_d(x) = F_g(x) = x^2$, a discrete form of Eq. (7) can then be $$H(\underline{a}) = [\hat{\underline{\tau}}(\underline{a}) - \underline{\tau}]^T W[\hat{\underline{\tau}}(\underline{a}) - \underline{\tau}] + G(\underline{a})^T V G(\underline{a}) \quad W = \{W_i \delta_{ij}\}$$
$$V = \{V_i \delta_{ij}\} \quad (21)$$

where any-one skilled in the art can introduce other norms according to Eq. (8, 9) In the procedure to minimize H(a) we start with a parameter vector a and add a variation vector $\underline{h}$, so small that we can use a 1st order Taylor expansion as $$H(\underline{a} + \underline{h}) = \left(\hat{\underline{\tau}}(\underline{a}) + \frac{\partial \hat{\underline{\tau}}}{\partial \underline{a}} \underline{h} - \underline{\tau}\right)^T W \left(\hat{\underline{\tau}}(\underline{a}) + \frac{\partial \hat{\underline{\tau}}}{\partial \underline{a}} \underline{h} - \underline{\tau}\right) + \quad (22)$$

$$\left(\underline{G}(\underline{a}) + \frac{\partial \underline{G}}{\partial \underline{a}} \underline{h}\right)^T V \left(\underline{G}(\underline{a}) + \frac{\partial \underline{G}}{\partial \underline{a}} \underline{h}\right)$$

Differentiation the above approximation of H(a+h) with respect to $\underline{h}$ and equating to zero gives $$\frac{\partial H}{\partial \underline{h}} = 2S_\tau(\underline{a})^T W[\hat{\underline{\tau}}(\underline{a}) - \underline{\tau}] + 2S_\tau(\underline{a})^T W S_\tau(\underline{a})\underline{h} + \quad (23)$$

$$2S_G(\underline{a})^T V G(\underline{a}) + 2S_G(\underline{a})^T V S_G(\underline{a})\underline{h} = 0$$

$$S_\tau(\underline{a}) = \frac{\partial \hat{\underline{\tau}}}{\partial \underline{a}} = \left(\frac{\partial \hat{\tau}_i}{\partial a_k}\right)$$

$$S_G(\underline{a}) = \frac{\partial \underline{G}}{\partial \underline{a}} = \left(\frac{\partial G_i}{\partial a_k}\right)$$

where $S_\tau(\underline{a})$ and $S_G(\underline{a})$ are the sensitivity matrices of the NPD model and the gradient model to variations in the parameter vector. When the connection points between the intervals are part of the parameters, the sensitivity matrices are conveniently estimated numerically. Eq. (23) is solved for $\underline{h}$, which gives the iteration scheme
which gives rise to the iterative estimation scheme as $$\underline{\alpha}_{n+1} = \underline{\alpha}_n + \underline{h}(\underline{\alpha}_n)$$

$$\underline{h}(\underline{a}) = [S_\tau(\underline{a})^T W S_\tau(\underline{a}) + S_G(\underline{a})^T V S_G(\underline{a})]^{-1} \cdot [S_\tau(\underline{a})^T W[\underline{\tau} - \hat{\underline{\tau}}(\underline{a})] - S_G(\underline{a})^T V G(\underline{a})] \quad (24)$$

Subject to constraints: $\beta_{min} < \alpha_{n+1,j} < \beta_{max}$ j=1, 2, . . . ,J where $\alpha_{n+1,j}$ is the (n+1)-th estimate of $\alpha_j = \beta_j$.

Observability of the parameter vector $\alpha$ is determined by the invertability of the matrix $S_\tau(\underline{a})^T W S_\tau(\underline{a})^T + S_G(\underline{a})^T V S_G(\underline{a})$, which is a standard analysis known to anyone skilled in the art. From FIG. 3 we see that adequately broad constraints for soft tissue estimates are $\beta_{min} \approx 1.5$ and $\beta_{max} \approx 3.1$.

With low noise in the HF receive signals used for determining $\tau_y(\underline{r},z)$, one can lean on the constraints in both in Eq. (20, 24). When the HF receive signals are dominated by multiple scattering noise, we can W=0 according to the discussion above.

Keeping the connection points between the intervals, I(j), constant gives a simplified version of the above algorithm. In this case the parameter vector reduces to $\underline{a} = \{\beta_j\}$, j=1 . . . , J, and the NPD model and gradient models can be written as linear matrix operators $\hat{\underline{\tau}}(\underline{a}) = A\underline{a}$ and $\underline{G}(\underline{a}) = G\underline{a}$, and the sensitivity matrices are $S_\tau(\underline{a}) = A$ and $S_G(\underline{a}) = G$.

The above illustrates that the functionals in Eqs. (7, 16, 21) can be minimized by a series of discrete algorithms by any-one skilled in the art. Averaging the results for neighboring transmit beams is also useful. The functionals in Eqs. (16, 19) can also by any-one skilled in the art be expanded to include neighboring transmit beams as given by the integral over $R_t$ in Eq. (7). Several other algorithms for minimizing H(a) can be introduced by anyone skilled in the art. We have in the parameter vector of Eq. (15) included the transition points of the parameter intervals. It can in some situations provide a more stable optimization by keeping a fixed set of intervals, and potentially allow for a larger number J of intervals. One can also introduce the number of parameter intervals J as a parameter to be part of the optimization, for example by extending the parameter vector in Eq. (15) to $$\underline{a} = \{a_k\} = \{\beta_1, \beta_2, \ldots, \beta_J, I(1), I(2), \ldots, I(J-1), J\}$$
$$K = 2J \quad (25)$$

The number of parameter intervals J can then be optimized as parts of the above estimation algorithms. It can help to carry through the optimization of the parameter vector in Eq. (15) for a set of given J values, and select the J value that gives lowest value of H(a) considering the computation time.

We note that the NPD estimated with the crossing transmit and receive beams can also be used in the processing of back-scattered HF signals obtained with a HF receive beam axis along or close to the HF transmit beam axis, as for example described in U.S. Pat. Nos. 7,641,613, 8,038,616, 8,550,998, 9,291,493 to suppress multiple scattering noise and estimate nonlinear scattering for received HF back-scatter signals. The back-scatter images have better spatial resolution in range, and is also the type of images currently in general use, while the cross beam method provides more accurate estimation of the spatial variation of the NPD and PFD with less influence from multiple scattering noise.

For good suppression of multiple scattering noise in the HF back-scatter receive signals, it is advantageous to use equal HF transmit and back-scatter receive beams, as described in U.S. Pat. No. 9,291,493. The temporal Fourier transform of a short depth interval of the 1st order HF back-scatter receive signal for an image pixel depth $z_k = ct_k/2$, where $t_k$ is the arrival time for the signal for that pixel, can be modeled as $$Y_p(z_k, \underline{r}_t, \omega) = U(\omega) \int d^2 r_{t1} H_t(z_k, \underline{r}_t - \underline{r}_{t1}, \omega)^2 \sigma_p(\underline{r}_{t1}) \quad (26)$$

where the combined HF back-scatter, $H_{be}$, and HF transmit, $H_t$, is $H_t H_{br} = H_t^2$ because the HF back-scatter receive beam and HF transmit beams are equal, shown as 601 in FIG. 6. The back-scatter observation cell in the z direction is defined by the HF pulse length, and is hence short.

A very useful synthetic focusing of the HF back-scatter receive signal can then be obtained by only transversal filtering of the HF back-scatter receive signal image at fixed depth as $$\hat{Y}_{pf}(z_k, \underline{r}_t, \omega) = U(\omega) \int d^2 r_{t2} W_{rt}(z_k, \underline{r}_t - \underline{r}_{t2}, \omega) Y_p(z_k, \underline{r}_{t2}, \omega) \quad (27)$$

$$= U(\omega) \int dz_1 d^2 r_{t1} H_f(z_k, \underline{r}_t - \underline{r}_{t1}, \omega) \sigma_p(\underline{r}_{t1})$$

$$H_f(z_k, \underline{r}_t, \omega) = \int d^2 r_{t2} W_{rt}(z_k, \underline{r}_t - \underline{r}_{t2}, \omega) H_t(z_k, \underline{r}_{t2}, \omega)^2$$

To minimize the width of $H_f$ in the transversal direction $\underline{r}_t$ we chose the filter kernel $W_{rt}$ so that the phase gradient of the Fourier transform $H_f$ in the transversal direction is zero. Denoting the Fourier transform in the transversal coordinates by $F_{rt}\{\ \}$ the convolution gives $$F_{rt}\{H_f(z_k,\underline{r}_t,\omega)\} = F_{rt}\{W_{rt}(z_k,\underline{r}_t,\omega)\} F_{rt}\{H_t(z_k,\underline{r}_t,\omega)^2\}$$

$$F_{rt}\{W_{rt}(z_k,\underline{r}_t,\omega)\} = A_{rt}(z_k,\underline{k}_t,\omega)e^{-i\varphi_{rt}(z_k,\underline{k}_t)} \varphi_{rt}(z_k, \underline{k}_t) = \angle F_{rt}\{H_t(z_k,\underline{r}_t,\omega)^2\} \quad (28)$$

where $\underline{k}_t$ is the Fourier coordinates in the transversal plane, and $A_{rt}$ is an apodization function to reduce side-lobes. In particular is the so-called Wiener type filter and the matched filter as $$F_{rt}\{W_{rt}(z_k, r_t, \omega)\} = \frac{1}{F_{rt}\{H_t(z_k, r_t, \omega)^2\}\{1 + \mu/|F_{rt}\{H_t(z_k, r_t, \omega)^2\}|^2} \quad (29)$$

$$F_{rt}\{W_{rt}(z_k, r_t, \omega)\} = (F_{rt}\{H_t(z_k, r_t, \omega)^2\})^*$$

where $\mu$ is a noise parameter to be adjusted for good performance in the practical situation. Eq (28.29) include both phase correction and apodization.

From the estimated $\hat{\beta}(\underline{r})$ from Eqs. (20, 24) we can in the processing unit 511 of FIG. 5 simulate $H_t(z_k,\underline{r}_t,\omega)$ with the spatially varying estimate of the linear propagation velocity $c_0(\underline{r}) = c_0[\hat{\beta}(\underline{r})]$ of Eq. (3). The filter kernels in Eqs. (28, 29) can then be applied in Eq. (27) by anyone skilled in the art to produce synthetically focused HF back-scatter receive signal with both suppression of multiple scattering noise and corrections of wave front aberrations through lateral filtering.

From an estimated value of $c_0(\underline{r}) = c_0[\hat{\beta}(\underline{r})]$ from Eq. (3), one can use these values to estimate array element signal delay and amplitude corrections for wave front aberrations produced in the heterogeneous medium for both the HF transmit and the HF cross-beam and backscatter receive beams [8,9]. We describe two methods for estimation of the delay and amplitude corrections for focusing the transmit and/or receive beams from an array aperture $S_{rf}$ onto the focal point $\underline{r}_f$. We assume $S_{rf}$ comprises a set of K elements out of the total number of elements in the array, where $\underline{r}_k$ is the center of array element #k.

In the first method we start by numerical simulation of the wave propagation from a point source in the focal point at $\underline{r}_f$ to the actual array aperture, through the heterogeneous object with spatially varying propagation velocity $c_0(\underline{r})$. We write the simulated wave function at the center $\underline{r}_k$ of array element #k as $g(\underline{r}_k,\underline{r}_f,\omega)$, where $\omega$ is the angular frequency of the point source at the focal point $\underline{r}_f$. We note that $g(\underline{r}_k,\underline{r}_f,\omega)$ is the Greens function for the point source at $\underline{r}_f$. We then filter the transmit pulse for each element by the filter $$H(\underline{r}_k,\underline{r}_f,\omega) = A(\underline{r}_k,\underline{r}_f) g(\underline{r}_k,\underline{r}_f,\omega)^* \quad k=1,\ldots,K \quad (30)$$

where $A(\underline{r}_k,\underline{r}_f)$ is a chosen amplitude apodization function of the transmit pulse across the actual aperture $S_{rf}$. The phase of g represents both the standard focusing delay for beam forming in a homogeneous medium, and together with the amplitude of g an optimal amplitude and delay correction for the wave front aberrations due to the spatially varying propagation velocity [8,9]. The major component of this filter is however the linear component of the phase that represents a delay correction for the wave front aberrations.

A less computer intensive approach can be obtained with ray acoustics techniques. We define $\bar{c}$ as the spatial average of $c_0(\underline{r})$ over the actual region in front of the array. The well-known differential equation for an acoustic ray $\underline{r}(s)$ that passes normal to the acoustic wave fronts, is given in [18] as $$\frac{d}{ds}\left(n\frac{d\underline{r}}{ds}\right) = \nabla n \quad (31)$$

$$n(\underline{r}) = \frac{\bar{c}}{c_0(\underline{r})}$$

where s is the arc-length along the ray (i.e. $\underline{r}(s)$ is a taxameter representation of the ray) and $n(\underline{r})$ is the spatially varying refractive index of the material. To focus the transmit or receive beams onto the focal point $\underline{r}_f$, we simulate numerically Eq. (31) for the acoustic ray $\underline{r}_{fk}(s)$ from the focal point $\underline{r}_f$ to the center $\underline{r}_k$ of array element #k. The beam steering delay for element #k is then calculated as $$\tau_f(\underline{r}_k, \underline{r}_f) = \frac{1}{\bar{c}}\left[al(\underline{r}_k, \underline{r}_f) - al(\underline{r}_0, \underline{r}_f)\right] \quad (32)$$

$$al(\underline{r}_k, \underline{r}_f) = \int_{\underline{r}_{fk}} ds\, n(\underline{r})$$

$$k = 1, \ldots, K$$

where $al(\underline{r}_k,\underline{r}_f)$ is the acoustic length of the acoustic ray $\underline{r}_{fk}(s)$ from $\underline{r}_f$ to $\underline{r}_k$.

For best results one should do 3D scanning of the beams to obtain 3D images of $c_0(\underline{r})$ as described above. For corrections of wave front aberrations, the array should with mechanical elevation scanning be of the 1.75D type with larger elements in the elevation direction used for beam focusing and aberration corrections. With a full matrix array, one obtain electronic focusing and beam steering both in the azimuth and elevation directions.

Note that with the synthetic focusing in Eqs. (27-29) we can use fixed focus HF transmit and receive beams both in the azimuth and the elevation direction, as the synthetic focusing is done through filtering of the HF receive signal image. The spatially varying $c_0(\underline{r})$ estimates could also be used as start parameters in iterative "bent ray" estimation procedures to estimate the spatially varying linear wave propagation velocity and absorption, for example according to tomographic methods [13-17].

The methods and instrumentation described above provides quantitative tissue images that opens for improved detection of tissue diseases, such as cancer and atherosclerotic plaques. It also opens for artificial intelligence (AI) detection and characterization of such diseases, when 3D data of the diseased tissue and some surrounding tissue is available.

Thus, while there have shown and described and pointed out fundamental novel features of the invention as applied to preferred embodiments thereof, it will be understood that various omissions and substitutions and changes in the form and details of the devices illustrated, and in their operation, may be made by those skilled in the art without departing from the spirit of the invention.

It is also expressly intended that all combinations of those elements and/or method steps, which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

REFERENCES

[1] U.S. Pat. No. 7,641,613,
[2] U.S. Pat. No. 8,038,616,
[3] U.S. Pat. No. 8,550,998,
[4] U.S. Pat. No. 9,291,493,
[5] U.S. Pat. No. 7,727,156,
[6] U.S. Pat. No. 8,182,428,
[7] U.S. patent application Ser. No. 15/821,211
[8] U.S. Pat. No. 6,905,465,
[9] U.S. Pat. No. 7,273,455,
[10] U.S. patent application Ser. No. 16/258,251,
[11] Hasgall P A, Di Gennaro F, Baumgartner C, Neufeld E, Gosselin M C, Payne D, Klingenböck A, Kuster N, "IT'IS Database for thermal and electromagnetic parameters of biological tissues," Version 3.0, Sep. 1, 2015, DOI: 10.13099/VIP21000-030. www.itis.ethz.ch/database https://www.itis.ethz.ch/virtual-population/tissue-properties/overview/
[12] Hartmann B: "Potential energy effects on the sound speed in liquids" J. Acoust. Soc. Am. 65(6), June 1979: 1392-1396.
[13] Kvam J, Solberg S, Myhre O F, Rodrigues-Morales, Angelsen B A J: "Nonlinear bulk elasticity imaging using dual frequency ultrasound". JASA 146.4(2019: 2492-2500
[14] Kvam J, Holm S, Angelsen B: "Exploiting Balou's rule for Better Tissue Classification". Proceeding Acoust Soc Am, May 14, 2018, http://dx.doi.org(DOI number)
[15] Hormati A, Jovanovi I, Roy O, Vetterli M: "Robust Ultrasound Travel-time Tomography Using the Bent Ray Model" Medical Imaging 2010: Ultrasonic Imaging, Tomography, and Therapy, Ed: J D'Hooge, S A McAleavey, Proc SPIE Vol. 7629, 762901
[16] Li C, Duric N, Littrup P, Huang L: "In Vivo Breast Sound-Speed Imaging with Ultrasound Tomography", Ultrasound Med Biol. 2009 October; 35(10) 1615-1628
[17] Opielinski K J, Pruchnicki P, Gudra T, Podgorski P, Krasnicki T, Kurcz J, Sasiadek M: "Ultrasound Transmission Tomography Imaging of Structure of Breast Elastography Phantom Compared to US, CT, and MRI." Archives of Acoustics, Vol. 38, No. 3, pp. 321-334 (2013)
[18] Opielinski K J, Pruchnicki P, Szymanowski P, Szeoieniec W K, Szweda H, Swis E, Jozwik M, Tenderenda M, Bulkowski M: "Multimodal ultrasound computer assisted tomography: An approach to the recognition of breast lesions." Computerized Medical Imaging and Graphics 65 (2018) 102-114
[19] Huang L, Shin J, Chen T, Lin Y, Intrator M, Hanson K, Epstein K, Sandoval D, Williamson M: "Breast ultrasound tomography with two parallel transducer arrays: Preliminary clinical results". Medical Imaging 2015: Ultrasound Imaging and Tomography, Ed: J. G. Bosch, N Duric, Proc. of SPIE Vol. 941916.
[20] Angelsen B A J: "Ultrasound Imaging—Waves, Signal, and Signal Processing". Emantec A S, Trndheim, Norway, Apr. 30, 2000

What is claimed is:

1. A method for estimating of locally varying nonlinear elastic parameters (NEPs) in a spatial estimation region (SER) of a material, from a set of measured nonlinear propagation delays (NPDs) as a function of position in said SER of the material, utilizing a mathematical model that from spatially varying NEP values in said SER produces spatially varying model NPDs in said SER, said method comprising:

a) measurement of the NPDs as a function of position in said SER through
transmitting at least two pulse complexes composed of overlapping low frequency (LF) and a high frequency (HF) pulses, along LF and HF transmit beams that overlap at least within said SER,
recording HF receive signals from scattered HF pulses from object structures within a set of depth regions along HF transmit beams within said SER from at least two transmitted pulse complexes with different LF pulses along the same HF transmit beam, and
comparing HF receive signals scattered from said HF pulses of pulse complexes with different LF pulses, from said set of depth regions along the same HF transmit beam, to produce estimates of said NPDs at said set of depth regions along said HF transmit beams in said SER, and b) forming an estimation functional (EF) that with a set of NEPs as input gives a weighted sum of i) a distance function of the difference between said measured NPDs and said model NPDs for said set of NEP values, weighted by a spatially variable distance weight, and ii) a measure of the local variation of said NEP values within said SERs weighted by a spatially variable variation weight, and where c) local values of said distance weight and said variation weight are estimated from one or both of i) an assessment of strong local reflectors in the received HF signals, and ii) an assessment of the local magnitude of multiple scattered HF noise relative to the local magnitude of the first order scattered HF signal, and d) for a given set of measured NPDs, minimizing said EF with respect to said set of NEPs, and using the set of NEPs that minimizes said EF to form an estimate of spatially varying NEPs within said SER.

2. The method according to claim 1, where said EF is minimized with respect to said set of NEPs subject to one or both of i) a maximal, and ii) a minimal value constraint on the estimated local NEPs, and using the set of NEPs that minimizes said EF subject to these value constrains, to form an estimate of spatially varying NEPs within said SER.

3. The method according to claim 1, where said distance weight is formed as a ratio of a narrow region average to a larger region average of the envelope of the received HF signals within said SER, and said variation weight is formed as a positive function of said distance weight, where the differential of said positive function is negative.

4. The method according to claim 1, where said assessment of the local magnitude of multiple scattered HF noise relative to the local magnitude of the first order scattered HF signal is obtained from the measured NPDs.

5. The method according to claim 4, where said assessment of the local magnitude of multiple scattered HF noise relative to the local magnitude of the first order scattered HF signal is obtained from the value of the measured NPDs, being below a fraction of an expected limit.

6. The method according to claim 1, where the HF receive signals for measuring the NPDs are obtained from one or both of i) a set of HF receive beams crossing the HF transmit beam at different depths along the HF transmit beam, and ii) using a HF receive beam with close to the same beam axis as the HF transmit beam, and gating intervals of the HF backscatter receive signal at different depths along the HF transmit beam.

7. The method according to claim 1, where said distance function is based on the function $f(x)$ of the value x of the difference between said measurement outputs and said model outputs in each point of said SER, and where the sign of the differential of $f(x)$ is equal to the sign of x.

8. The method according to claim 1, where said measured NPDs are, after further processing, used for corrections of said HF receive signals for each transmit beam to produce corrected HF receive signals for each transmit beam, and at least two corrected HF receive signals are for each transmit beam combined to form one or both of i) HF receive signals with suppression of multiple scattering noise, and ii) HF receive signals where linear scattering is suppressed and nonlinear scattering is enhanced.

9. The method according to claim 1, where synthetic lateral focusing of the HF receive range cell is obtained at a multitude of depths through lateral filtering of the HF receive signals for multiple transmit beams using a set of filter coefficients, where said filter coefficients are determined through calculations of the product of said HF transmit and receive beams using an ultrasound propagation velocity that is one of i) constant in space, and ii) a function of said estimate of the spatially varying NEPs.

10. The method according to claim 1, where determination of the distance weight and the variation weight is done through machine learning in the form of differential programming on the received HF signals in relation to the type of material object studied.

11. A method for estimating locally varying nonlinear elastic parameters (NEPs) in a spatial estimation region (SER) of a material, from a set of measured nonlinear propagation delays (NPDs) as a function of position in said SER of the material, utilizing a mathematical model that from spatially varying NEP values in said SER produces spatially varying model NPDs in said SER, said method comprising:
 a) (i) measuring the NPDs as a function of position in said SER by transmitting at least two pulse complexes composed of overlapping low frequency (LF) and high frequency (HF) pulses along LF and HF transmit beams that overlap at least within said SER, and (ii) recording HF receive signals from scattered HF pulses from object structures within a set of depth regions along HF transmit beams within said SER from at least two transmitted pulse complexes with different LF pulses along each HF transmit beam, and comparing HF receive signals scattered from said HF pulses of pulse complexes with different LF pulses from said set of depth regions along the same HF transmit beams, to produce estimates of said NPDs at said set of depth regions along said HF transmit beams in said SER, and
 b) forming an estimation functional (EF) that with a set of NEPs as input gives a weighted sum of
 i) a distance function of the difference between said measured NPDs and said model NPDs for said set of NEP values, weighted by a spatially variable distance weight, and
 ii) a measure of the local variation of said set of NEP values within said SERs weighted by a spatially variable variation weight, and where
 b) for a given set of measured NPDs, minimizing said EF with respect to said set of NEPs, and using the set of NEPs that minimizes said EF to form an estimate of spatially varying NEPs within said SER.

12. An instrument for estimating locally varying nonlinear elastic parameters (NEPs) in a spatial estimation region (SER) of a material, from a set of measured nonlinear propagation delays (NPDs) as a function of position in said SER of the material, utilizing a mathematical model that from spatially varying NEP values in said SER produces spatially varying model NPDs in said SER, said instrument comprising:
 a) multi-element ultrasound wave transmit and receive means comprising multiple ultrasound transmit and receive elements, the multi-element ultrasound wave transmit and receive means being configured to permit:
  transmitting overlapping low frequency (LF) and high frequency (HF) pulses along LF and HF transmit beams that overlap at least within said SER, and
  receive HF element receive signals from scattered HF pulses from object structures within said SER from at least two transmitted pulse complexes with different LF pulses along each HF transmit beam, and
 b) multi-channel electronic transmit and receive means configured to generate electronic HF and LF drive signals for said multi-element ultrasound wave transmit and receive means for transmitting said LF and HF pulse complexes, and receiving HF element receive signals from said multi-element ultrasound wave transmit and receive means, and
 c) first transfer means configured to transfer said HF element receive signals to an HF receive beam-forming means, the HF receive beam-forming means configured to form HF receive signals from a multitude of depths along the HF transmit beams,
 e) second transfer means configured to transfer said HF receive signals to an NPD measurement means, the NPD measurement means, configured to compare HF receive signals for said multitude of depths along each HF transmit beam from at least two different pulse complexes with differences in the LF pulse, to provide measured NPDs for said multitude of depths along said HF transmit beams, and
 g) third transfer means configured to transfer said measured NPDs to an estimating means, the estimating means configured to estimate the spatially varying NEPs within said SER from said measured NPDs, said estimating means being further configured to form an estimation functional (EF) that with a set of NEPs as input gives a weighted sum of i) a distance function of the difference between said measured NPDs and said model NPDs for said NEP values, weighted by a spatially variable distance weight, and ii) a measure of the local variation of said NEP values within said SERs weighted by a spatially variable variation weight, and for a given set of measured NPDs, minimize said EF with respect to said set of NEPs, and using the set of NEPs that minimizes said EF to form an estimate of spatially varying NEPs within said SER.

13. The instrument according to claim 12, where determination of the distance weight and the variation weight is done through machine learning in the form of differential programming on the received HF signals in relation to the type of material object studied.

14. The instrument according to claim 12, where said estimating means is further configured to estimate local values of said distance weight and said variation weight from one or both of i) an assessment of strong local reflectors in the received HF signals, and ii) an assessment of the local magnitude of multiple scattered HF noise relative to the local magnitude of the first order scattered HF signal.

15. The instrument according to claim 12, where said HF receive beam-forming means is configured to obtain said HF receive signals from a multitude of depths along the HF transmit beams through one or both of i) from a set of HF receive beams that crosses said HF transmit beams at said multitude of depths, and ii) gating intervals at said multitude of depths of a backscattered HF signal from a HF receive beam with beam axis close to the beam axis of said transmit beams.

16. The instrument according to claim 12, including means for further processing said measured NPDs, said means for further processing being configured to correct said HF receive signals for each transmit beam to produce corrected HF receive signals for each transmit beam, and at least two corrected HF receive signals are for each transmit beam combined to form one or both of i) HF receive signals with suppression of multiple scattering noise, and ii) HF receive signals where linear scattering is suppressed and nonlinear scattering is enhanced.

17. The instrument according to claim 12, further comprising synthetic focusing means configured to perform synthetic focusing of the HF receive range cell at a multitude of depths through lateral filtering of the HF receive signals for multiple transmit beams.

18. The instrument according to claim 12, further comprising weighting means configured to determine the distance weight and the variation weight through machine learning in the form of differential programming on the received HF signals in relation to the type of material object studied.

19. The instrument according to claim 12, wherein at least two of the first transfer means, second transfer means and third transfer means comprise a single transfer means.

\* \* \* \* \*